US008197276B2

(12) United States Patent
Egloff et al.

(10) Patent No.: US 8,197,276 B2
(45) Date of Patent: Jun. 12, 2012

(54) LOW PROFILE CONNECTOR SYSTEM

(75) Inventors: Eric Egloff, Lausaune (CH); Nicolas Fontaine, Bottens (CH)

(73) Assignee: DJO, LLC, Vista, CA (US)

( * ) Notice: Subject to any disclaimer, the term of this patent is extended or adjusted under 35 U.S.C. 154(b) by 0 days.

(21) Appl. No.: 12/856,382

(22) Filed: Aug. 13, 2010

(65) Prior Publication Data

US 2012/0040544 A1 Feb. 16, 2012

(51) Int. Cl.
H01R 11/22 (2006.01)

(52) U.S. Cl. ........................................ 439/268

(58) Field of Classification Search ............ 439/268, 439/909, 869, 860
See application file for complete search history.

(56) References Cited

U.S. PATENT DOCUMENTS

| | | | |
|---|---|---|---|
| 1,428,358 A | 9/1922 | Burbery | |
| 3,895,635 A * | 7/1975 | Justus et al. | 606/32 |
| 4,040,697 A | 8/1977 | Ramsay et al. | |
| 4,178,052 A | 12/1979 | Ekbom et al. | |
| 4,253,721 A * | 3/1981 | Kaufman | 439/372 |
| 4,268,101 A | 5/1981 | Stone | |
| 4,390,223 A | 6/1983 | Zenkich | |
| 4,671,591 A | 6/1987 | Archer | |
| 4,690,144 A | 9/1987 | Rise et al. | |
| 5,277,613 A | 1/1994 | Neward | |
| 5,326,272 A * | 7/1994 | Harhen et al. | 439/86 |
| 5,466,017 A | 11/1995 | Szabo et al. | |
| 5,498,235 A * | 3/1996 | Flower | 604/20 |
| 5,562,607 A * | 10/1996 | Gyory | 604/20 |
| 5,562,707 A | 10/1996 | Prochazka et al. | |
| 5,895,298 A * | 4/1999 | Faupel et al. | 439/729 |
| 5,895,369 A * | 4/1999 | Flower | 604/20 |
| 6,142,949 A * | 11/2000 | Ubby | 600/508 |
| 6,445,955 B1 | 9/2002 | Michelson et al. | |
| 6,687,536 B1 * | 2/2004 | Beck et al. | 604/20 |
| 7,066,767 B2 * | 6/2006 | Liao | 439/639 |
| 7,214,107 B2 * | 5/2007 | Powell et al. | 439/729 |
| 7,255,609 B1 * | 8/2007 | Epstein | 439/729 |
| 7,270,580 B2 | 9/2007 | Bradley et al. | |
| 7,364,440 B2 | 4/2008 | Gobron et al. | |
| 7,574,262 B2 * | 8/2009 | Haugland et al. | 607/49 |
| 2004/0039275 A1 | 2/2004 | Sato et al. | |

(Continued)

FOREIGN PATENT DOCUMENTS

FR 964611 5/1950

(Continued)

OTHER PUBLICATIONS

Extended European Search Report dated Dec. 14, 2010 in European Patent Application No. 09700152.3-2305/2237831.

(Continued)

Primary Examiner — Tulsidas C Patel
Assistant Examiner — Harshad Patel
(74) Attorney, Agent, or Firm — Ropes & Gray LLP

(57) ABSTRACT

A low-profile electrical connector includes a housing having exterior perimeter sides and top and bottom surfaces, where the bottom surface is configured to extend along a user's body site and the top surface is spaced above the bottom surface. The connector also includes a side-entry guide channel disposed along the bottom surface. The channel includes an opening along the exterior perimeter side that is configured to receive an electrically conductive element. The channel is also configured to guide the electrically conductive element within the housing. The connector includes a receptacle positioned within the housing and forms an electrically conductive interface with the electrically conductive element.

39 Claims, 19 Drawing Sheets

U.S. PATENT DOCUMENTS

| | | |
|---|---|---|
| 2004/0072475 A1 | 4/2004 | Istvan |
| 2004/0106964 A1 | 6/2004 | Fischer, Sr. et al. |
| 2005/0107841 A1 | 5/2005 | Meadows et al. |
| 2005/0131506 A1 | 6/2005 | Rezai et al. |
| 2005/0181341 A1 | 8/2005 | Ewing et al. |
| 2006/0195152 A1 | 8/2006 | Gerber |
| 2007/0088419 A1 | 4/2007 | Fiorina et al. |
| 2007/0191912 A1 | 8/2007 | Fischer et al. |
| 2008/0254684 A1* | 10/2008 | Tracy et al. ............. 439/620.21 |
| 2009/0149731 A1 | 6/2009 | Selvitelli et al. |
| 2009/0182393 A1 | 7/2009 | Bachinski |
| 2009/0182394 A1 | 7/2009 | Bachinski |

FOREIGN PATENT DOCUMENTS

| | | |
|---|---|---|
| GB | 257145 A | 8/1926 |
| WO | WO-01/03768 | 1/2001 |
| WO | WO-2006113801 A2 | 10/2006 |
| WO | WO-2009/148595 A2 | 12/2009 |

OTHER PUBLICATIONS

International Search Report and Written Opinion dated Dec. 20, 2011 in International Application No. PCT/US2011/047398.

International Search Report and Written Opinion dated Jan. 7, 2009 in International Application No. PCT/US2009/000082.

* cited by examiner

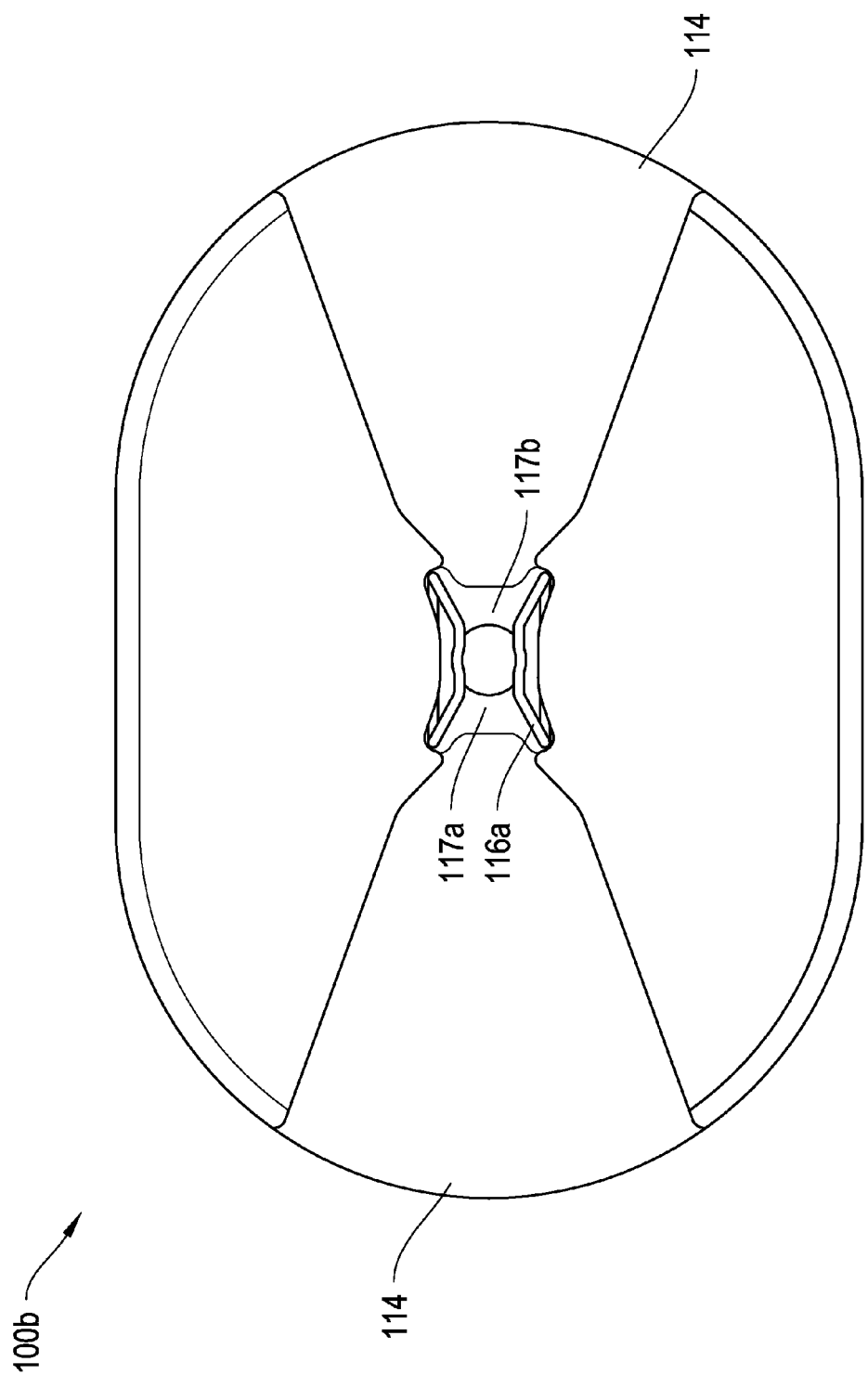

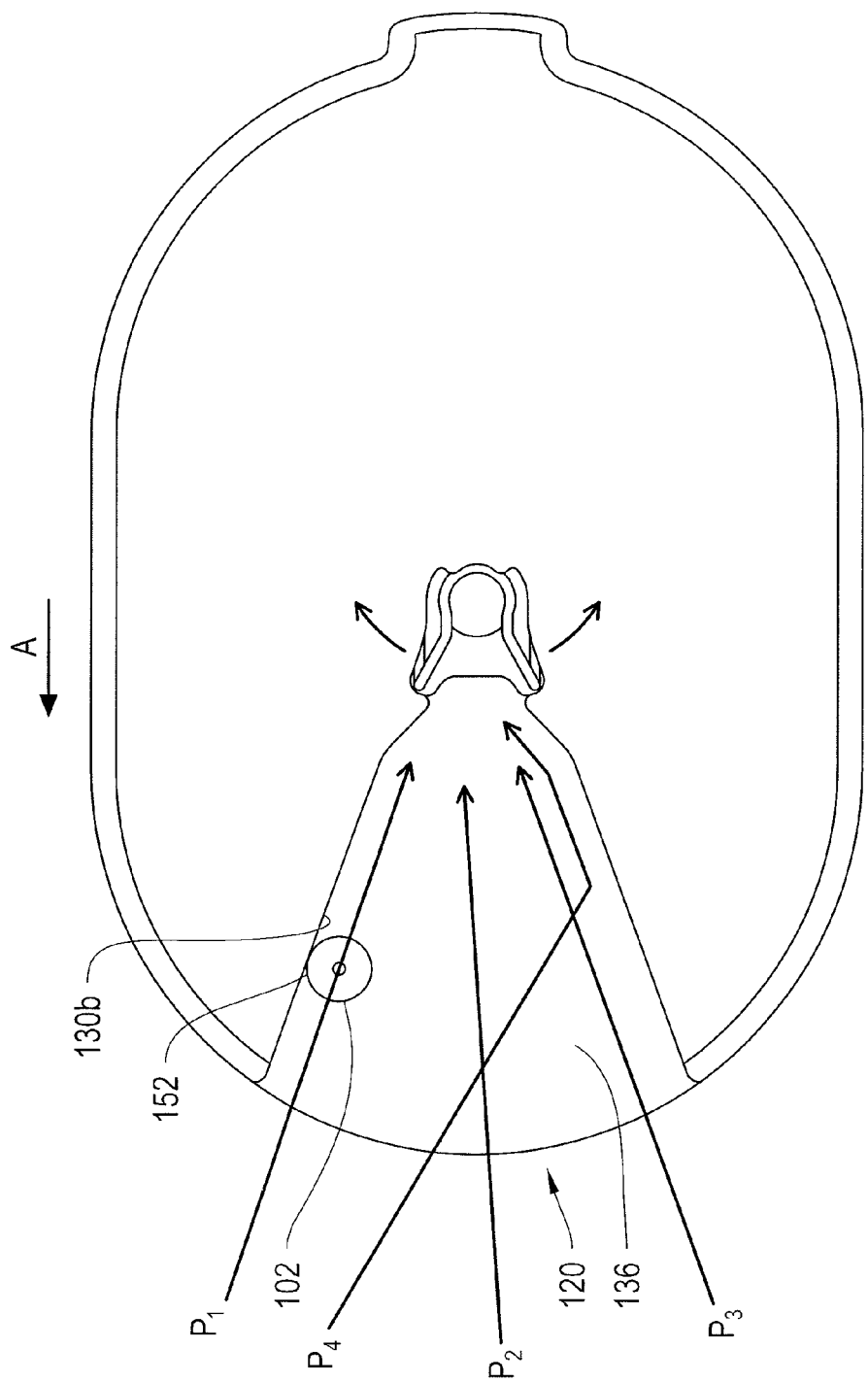

LOW PROFILE CONNECTOR SYSTEM

BACKGROUND

Electro-stimulation is widely used for pain relief, for muscle strengthening and conditioning, wound healing, and other medical rehabilitative and prophylactic purposes. An electrode (e.g., adhesive electrode) is placed on a user's skin near where the treatment is sought. In currently available systems, the electrode is connected to a wire that connects to a stimulator. Current devices tend to be bulky and have wires that get tangled or in the way of the user, which is intrusive to the user's daily activities. Due to the bulkiness of the device, it is also difficult to wear the device under clothing.

In addition, many current devices are complex and lack a simple, user-friendly connection mechanism between the stimulation device and an electrode to allow the user to easily connect or disconnect the device. The drawbacks of current electro-stimulation devices prevent the user from seamlessly integrating electrical stimulation therapy into their everyday lives. Also, if the electrode is placed in a hard to reach or non-visible body part (e.g., back of a patient's thigh), many devices are ill-equipped for seamless connection between the electrode and the stimulator device. As a result of the foregoing problems, user compliance is often poor.

One additional acute problem with existing connectors is that they are typically applied using a vertical connecting force. A vertical force can be painful when applied to electrodes used to treat tissue that has been burned or otherwise injured or subject to pain.

SUMMARY

The systems and methods described herein address the deficiencies in the prior art by providing low profile electrical connectors for connecting to an electro-stimulation interface having an improved connection mechanism that is easier to use, less intrusive to the user's daily activities, and less painful to apply to injured tissue. Methods of manufacturing such connectors are also disclosed. In general, the systems disclosed herein provide an electrical connector having a first side-entry portal as part of the connector housing, which portal receives an electrically conductive element, such as an electrode, and guides it within the housing along a path that generally extends parallel to the user treatment site. That configuration facilitates a lower profile connection system that is easier to use and also potentially less painful to users who have suffered severe burns or other injuries or pain. In exemplary systems a low profile electrical connector is provided with a housing having exterior perimeter sides, top and bottom surfaces and a side-entry guide channel disposed along the bottom surface. An opening configured to receive the electrically conductive element is disposed along the exterior perimeter side and in communication with the channel. The channel guides the electrically conductive element within the housing. The connector also includes a receptacle positioned within the housing and having an electrically conductive surface that forms an interface with the electrically conductive element. In certain implementations, the connector includes a plurality of side-entry portals along an exterior perimeter side for receiving the electrically conductive element. In certain implementations, the housing includes a transceiver that is configured to receive and/or transmit signals to a control device for stimulating muscle or nerve. The low-profile connector system described herein is configured to laterally engage the electrically conductive element. The connector system is preferably configured to be controlled wirelessly. In certain implementations, a plurality of connector systems are used, which may be connected by a flexible cable or wire. Additionally, the improved connector system allows a user with sensitive skin or wound to connect the stimulation device to the electrically conductive element positioned on sensitive skin areas without applying vertical connecting force.

In certain systems, the connector also includes a release actuator that is operatively engaged to the receptacle and configured to extend a force along a plane substantially parallel with the guide channel to disengage the electrode or other electrically conductive element from the receptacle. Upon actuating the release actuator, the electrically conductive element is removed from the receptacle when the housing is pulled away from the electrically conductive element along the guide channel.

In certain implementations, the side-entry guide channel may be formed at least in part by an interior wall that extends from the opening towards the receptacle. In certain implementations, pulling the receptacle away from the electrically conductive element along the guide channel disengages and removes the electrically conductive element from the receptacle. Optionally, the guide channel is defined at least in part by the bottom surface of the housing, and during disengagement the housing is pulled away from the electrically conductive element along an interior wall. The guide channel may include a path that tapers within the receptacle.

Optionally and alternatively, the receptacle of the connector includes one or more compressible legs that are operable by a release actuation to adjust the size of the channel and, thereby, insertion and release of the electrically conductive element. In certain implementations, the connector includes an upper leg, a vertically disposed post leg, and a leading leg configured to guide the electrically conductive element from the side-entry guide channel. The vertically disposed post legs are spaced apart from one another and configured to maintain space between the legs throughout operation. In certain implementations, a connector is provided with a release actuator configured to release the electrically conductive element from the receptacle. The release actuator is laterally engaged to the receptacle and adapted to move the upper legs of the receptacle away from one another in response to the actuation of the release actuator. In certain implementations, the side-entry guide channel extends between the leading leg and the upper leg.

Methods of assembling and using an electro-stimulation connector according to the disclosed technology are also provided.

Various alternative embodiments and sub-features are also disclosed herein with respect to the low profile electrical connectors, as will become apparent in the following description.

BRIEF DESCRIPTION OF THE DRAWINGS

The following figures depict illustrative embodiments in which like reference numerals refer to like elements. These depicted embodiments may not be drawn to scale and are to be understood as illustrative and not as limiting.

FIG. 2C shows a bottom view of an alternative embodiment of an exemplary electrode connector.

FIGS. 6A-6C show various views of an electrode connector engaging an electrode, according to illustrative embodiments.

DESCRIPTION OF EXEMPLARY EMBODIMENTS

The systems and methods described herein provide connection systems that allow a simple yet effective connection between electrically conductive element, such as an electrode, and an electro-stimulation device. In particular, a low-profile connector that laterally engages an electrically conductive element (such as a snap electrode) is described. A lateral connection allows a clinician or user to engage the low-profile connector to an electrically conductive element placed on a user's body site by applying a force parallel directly to the body site. This may be particularly useful and beneficial to users with sensitive skin such as post-operative or burn patients.

To provide an overall understanding, certain illustrative embodiments will now be described, as more particularly set forth in the figures. However, one of ordinary skill in the art will understand that the systems and methods described herein may be adapted and modified for other suitable applications, and that such other additions and modifications are within the scope hereof.

Figure 1A:
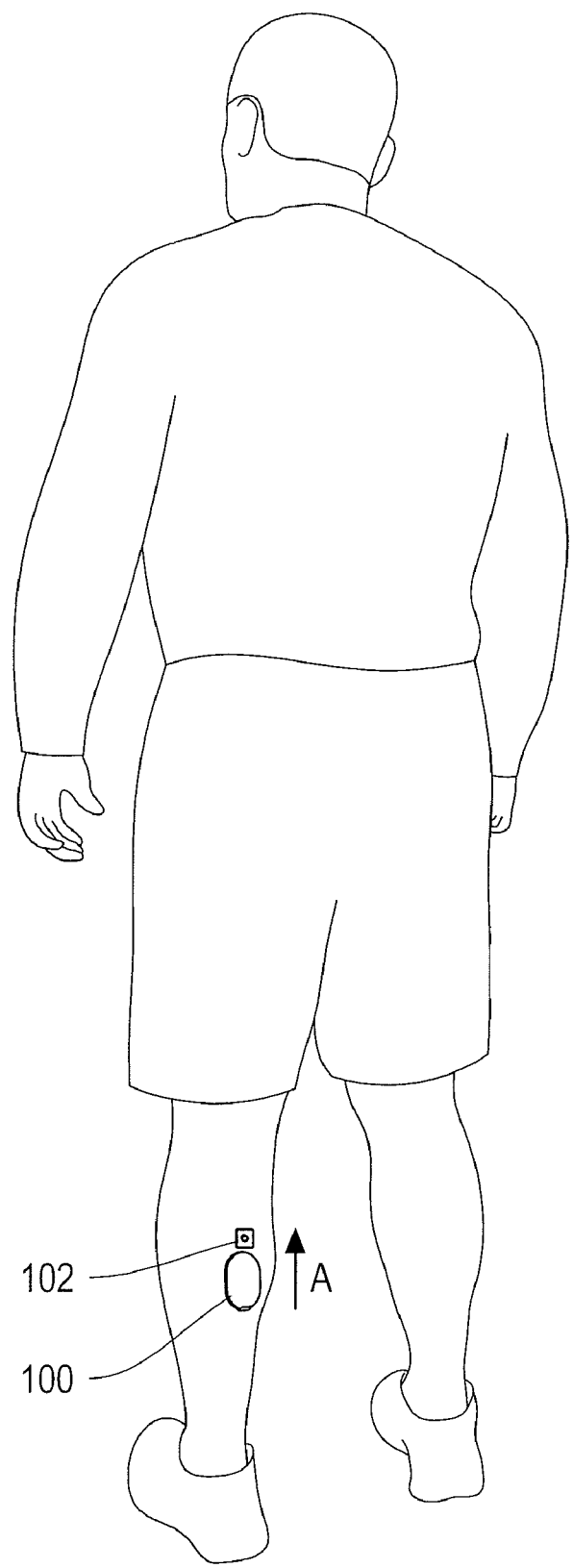
FIG. 1A depicts an electrode placed on a user's body and a connector configured to engage the electrode.

Turning to the illustrative embodiments, FIG. 1A shows an exemplary embodiment of a low profile connector 100 positioned to laterally engage an electrically conductive element 102 placed on the back of a user's calf. Some users may have difficulty connecting the connector 100 to electrodes or other electrically conductive elements placed in areas that are not easily visible or accessible. The connector 100 engages the electrically conductive element 102 along the surface of the user's skin in direction noted by Arrow A. Connection along that path may be easier to perform than along a vertical path.

Figure 1B:
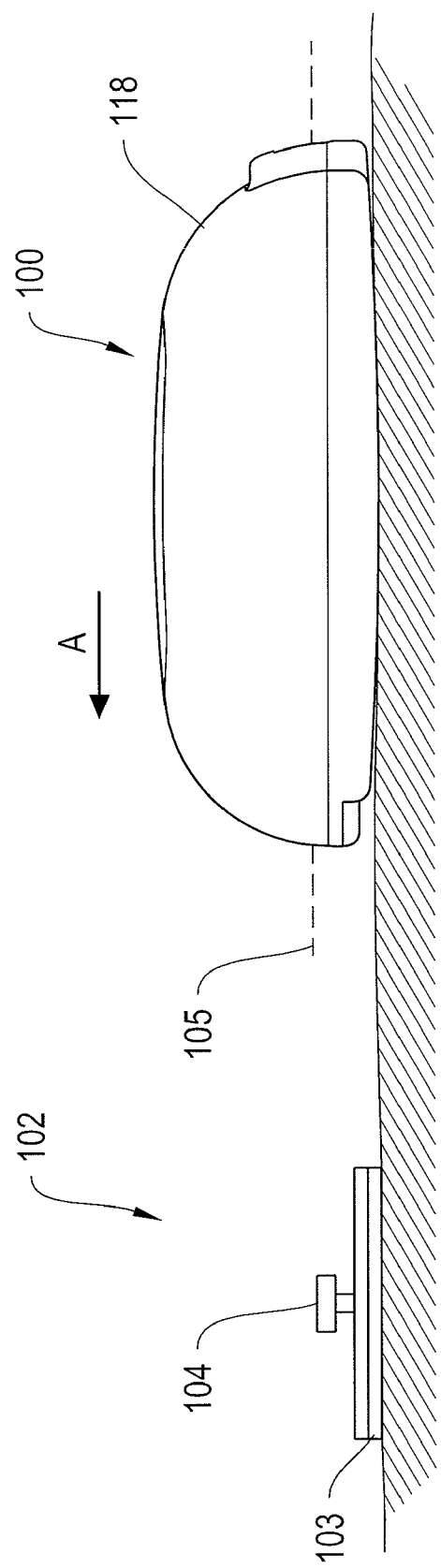
FIG. 1B depicts an exemplary mating relationship between the electrode and the connector of FIG. 1A.

As shown in FIG. 1B, the electrically conductive element 102 is a snap-type electrode having an active surface 103 which may be coated with a self-adhesive material or self-adhesive film (not shown) that sticks to a user's body site. The element 102 may alternatively be a sensor, or other conductive element, such as conductive embroidery in a user's clothing, provided it is positioned and configured with a stud or other conductive interface that enables it to make electrical contact with the connector 100. Exemplary conductive embroidery elements may include silver, copper or other metal (or conduct polymer) sewn or glued to the surface of a user garment, such as an exercise sock, t-shirt, or a brace, and having a stud or other conductive surface exposed and positioned to mate with the connector 100. In certain implementations, the electrode 102 is manufactured to have metallic or other conductive extensions from its sides, which extensions fit within pockets in the garment or are sewn within the garment, while the stud remains exposed for connection to the connector 100. The electrically conductive element shown as element (depicted as an electrode) 102 may be disposable or reusable depending on a particular treatment protocol or condition to be treated. The electrode 102 also includes a stud portion 104 that protrudes from the active surface 103 for making electrical connection with the connector 100. The connector 100 is depicted in FIG. 1B in relation to a plane 105 that extends axially through the connector and substantially parallel to the user's body site. As shown in FIG. 1B, the connector 100 travels laterally along the plane 105 in direction A until the electrode 102 engages within the connector 100. In certain implementations the connector contacts the user's tissue during lateral engagement, while in others the connector moves parallel to the user's body site but remains above it, without contacting the body site.

Figure 2A:
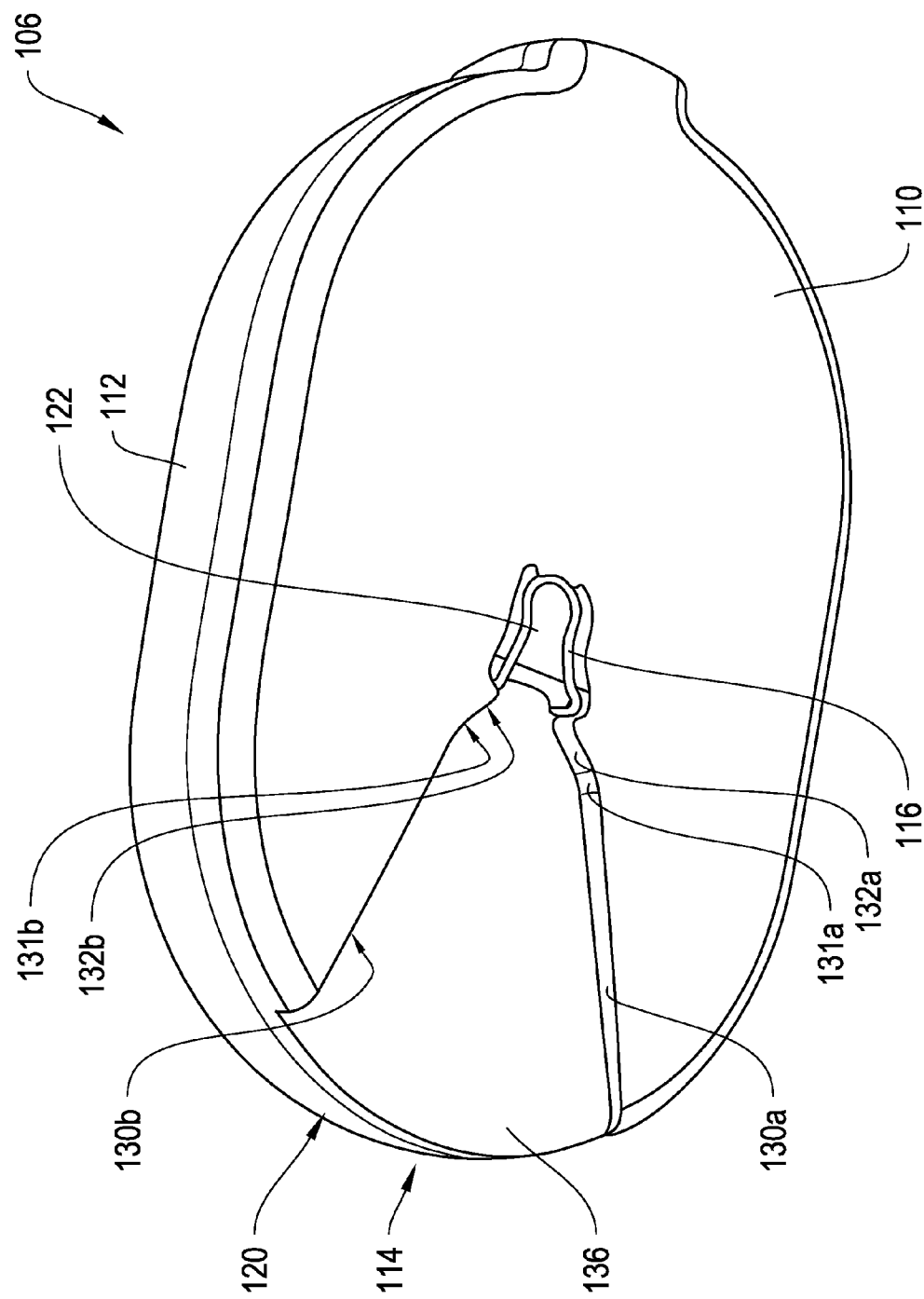
FIG. 2A shows a bottom-perspective view of an exemplary electrode connector.

As shown in FIG. 2A, a bottom-perspective view of the connector 100, the connector 100 includes a housing 106 having exterior perimeter side 112 that extend around the perimeter of the housing 106, a bottom surface 110 configured to extend along or parallel to a user's body site (such as the skin surface), and a top surface 108 spaced above the bottom surface 110. The connector 100 also includes a side-entry guide channel 114 defined at least in part by the bottom surface 110 of the housing 106. The guide channel 114 is adapted to self-guide the connector 100 with respect to the electrode 102. The guide channel 114 includes an opening 120 positioned along the exterior perimeter side 112 for receiving and guiding the electrode 102 within the housing 106. The guide channel 114 extends from the opening 120 to a receptacle pocket 122 of the housing 106. The receptacle pocket 122 houses a receptacle 116 and is formed on the bottom surface 110 of the housing 106. The receptacle 116 is disposed within the housing 106 and includes an electrically conductive element that receives the electrode 102 forming an electrical/mechanical connection between the electrode 102 and the connector 100, as described more fully below.

Figure 2B:
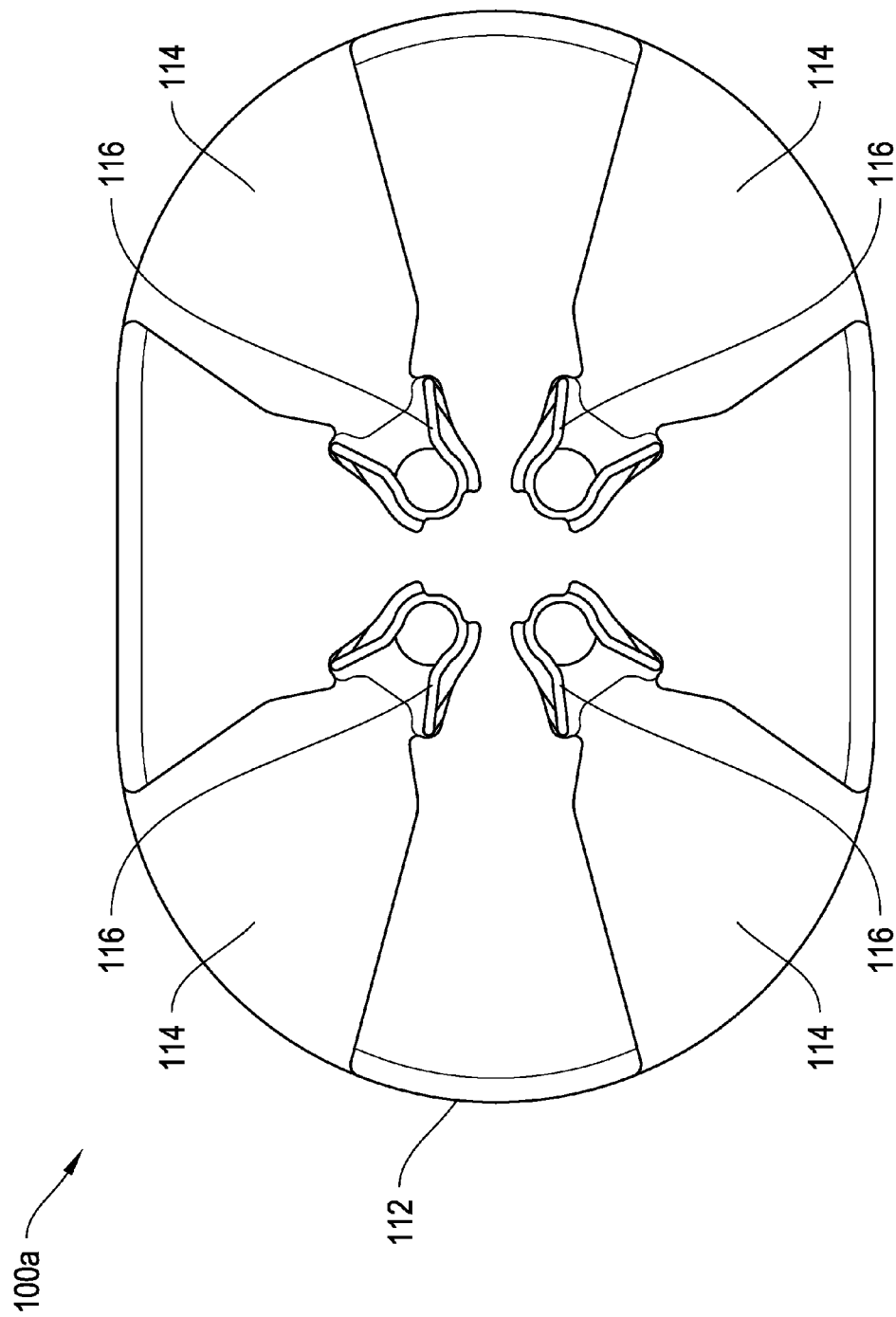
FIG. 2B shows a bottom view of an alternative embodiment of an exemplary electrode connector.

In certain implementations, the connector includes more than one side-entry guide channel. For example, as shown in FIG. 2B, which shows a bottom view of an alternative embodiment of the connector 100, a connector 100a includes a plurality of guide channels 114 disposed along the exterior perimeter side 112 for receiving an electrically conductive element such as an electrode. Although shown with four guide channels 114-114 in FIG. 2B, the connector 100a may include two, three or more guide channels depending on the treatment protocol or condition to be treated. Having a plurality of guide channels allows the user to engage an electrically conductive element (e.g., an electrode) in multiple ways, which may improve usability and user satisfaction. Variations on the structure of one or more of the guide channels may be made, as desired for adaptation to particular systems. For example, multiple such channels may connect to a single receptacle that can receive the electrode from any of the channels. FIG. 2C illustrates an example having a connector 100b including a plurality of guide channels 114 leading to a single receptacle 116a. The receptacle 116a includes first and second openings 117a and 117b, respectively, for receiving an electrically conductive element such as an electrode.

Figure 3:
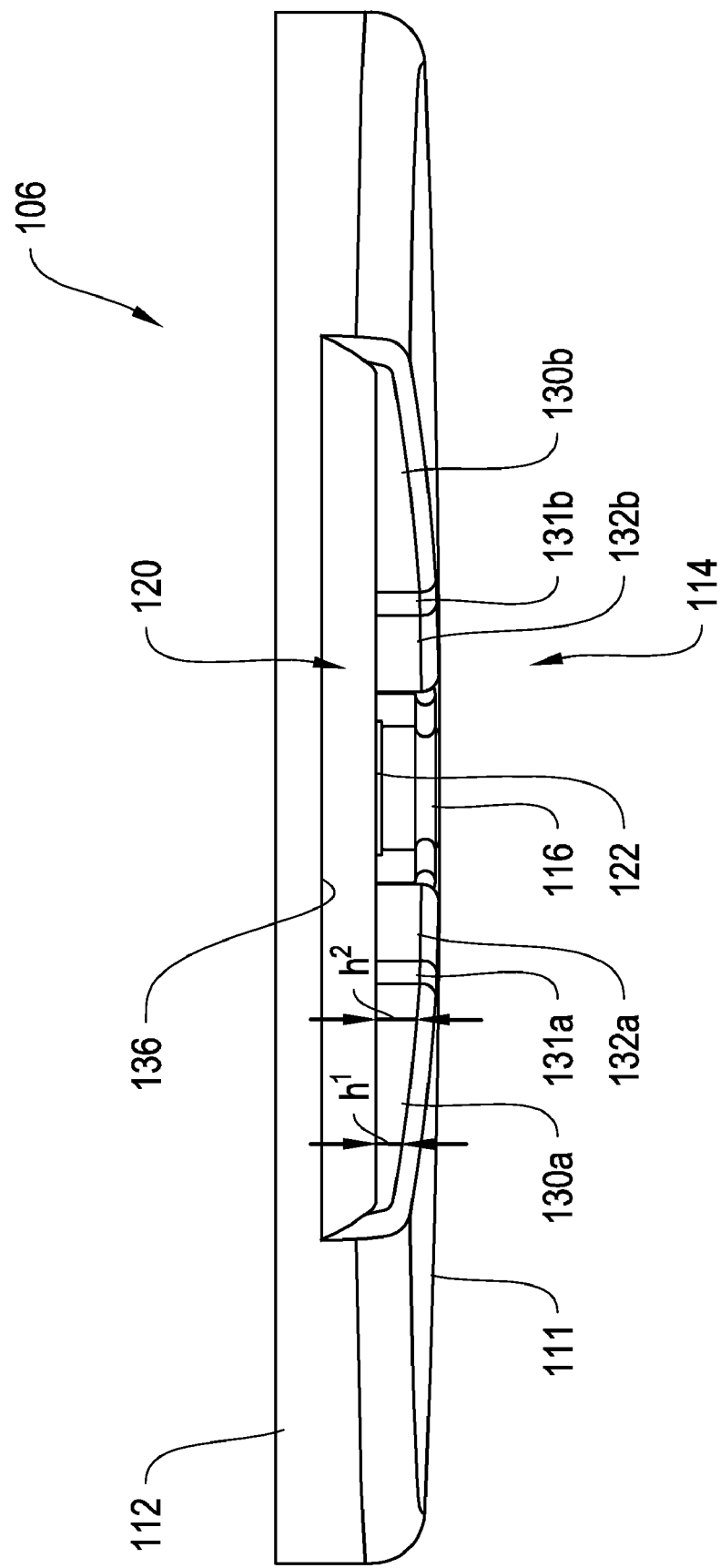
FIG. 3 shows a front view of the connector of FIG. 2A.

The side entry guide channel 114 is defined at least in part by the interior walls 130a and 130b that extend from the opening 120 towards the receptacle 116. As shown, the interior walls 130a and 130b form a V-shaped path that tapers into the receptacle 116. Such configuration allows the user to guide the electrode 102 within the housing 106, as the interior walls 130a or 130b slide against the stud 104 when the housing 106 moves laterally in direction A (as shown in FIG. 1B). The guide channel 114 also includes angled regions 132a and 132b of walls 130a and 130b, respectively, that further guide the electrode within the housing 106. FIG. 3, which depicts a front view of the housing 106, shows the angled wall regions 132a and 132b extending from respective end points 131a and 131b of the respective interior walls 130a and 130b to the receptacle pocket 122. The angled walls 132a and 132b receive the stud 104 as the stud 104 travels along the interior wall 130a or 130b and further guide the stud 104 into the receptacle 116. As shown, the height $h_1$ of the interior walls 130a and 130b increases from the opening 120 to height $h_2$ near the angled walls 132a and 132b. This ramped configuration creates a deeper channel for receiving and guiding the electrode 102 as the electrode 102 travels towards the receptacle 116. The guide channel 114 also includes an upper guiding surface 136 that is partly defined by the interior and angled walls. The upper guiding surface 136 and the interior and angled walls form a space for receiving and guiding the electrode 102 within the connector 100. The upper guiding surface 136 may extend at an angle with respect to the bottom surface 110 of the housing 106, or it may also extend substantially parallel to the bottom surface 110 of the housing 106.

In certain implementations, the housing 106 includes an angled bottom surface 111 that coextends with the bottom surface 110. In certain implementations, the angled bottom surface 111 slopes upwardly from the middle portion of the housing 106 towards the opening 120. FIG. 3 shows an embodiment of the angled bottom surface 111. The angled bottom surface 111 may allow the user to better engage the electrode 102 by allowing for more ergonomic placement of the connector 100. For example, when the user first places and slides the angled bottom surface 111 against the user's skin surface, the user may hold the connector 100 at an angle with respect to the user's skin surface. This may be more natural or ergonomic to some users.

Figure 4:
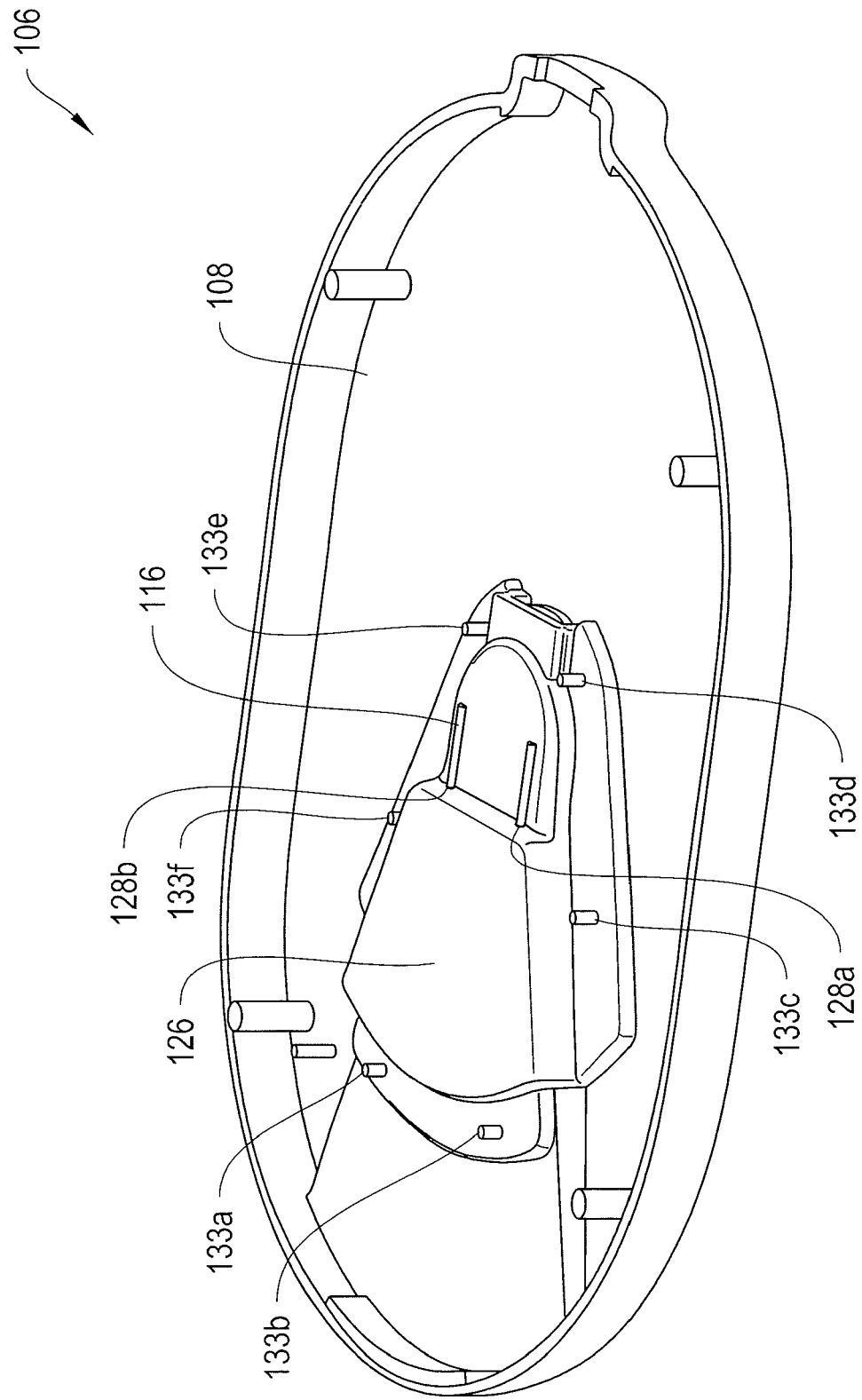
FIG. 4 shows a top-perspective view of the connector of FIG. 3 without a top cover.

FIG. 4 shows a top-perspective view of the housing 106. For clarity, the housing 106 is shown without the inner electronic components (e.g., PCB, battery). The housing 106 includes a receptacle connector 126 that connects the receptacle 116 to the housing 106. As shown, the receptacle connector 126 is a separate component and includes holes 128a and 128b that receive the receptacle to the housing 106. The receptacle connector 126 is also shaped to follow the contour of the top surface 108 of the housing 106. The receptacle connector 126 mates with a plurality of positioning posts 133a-133f, which are affixed to the housing 106. The receptacle connector 126 may be made of metallic material that can transfer electrical pulses from a controller (not shown) to the receptacle 116.

Figure 5:
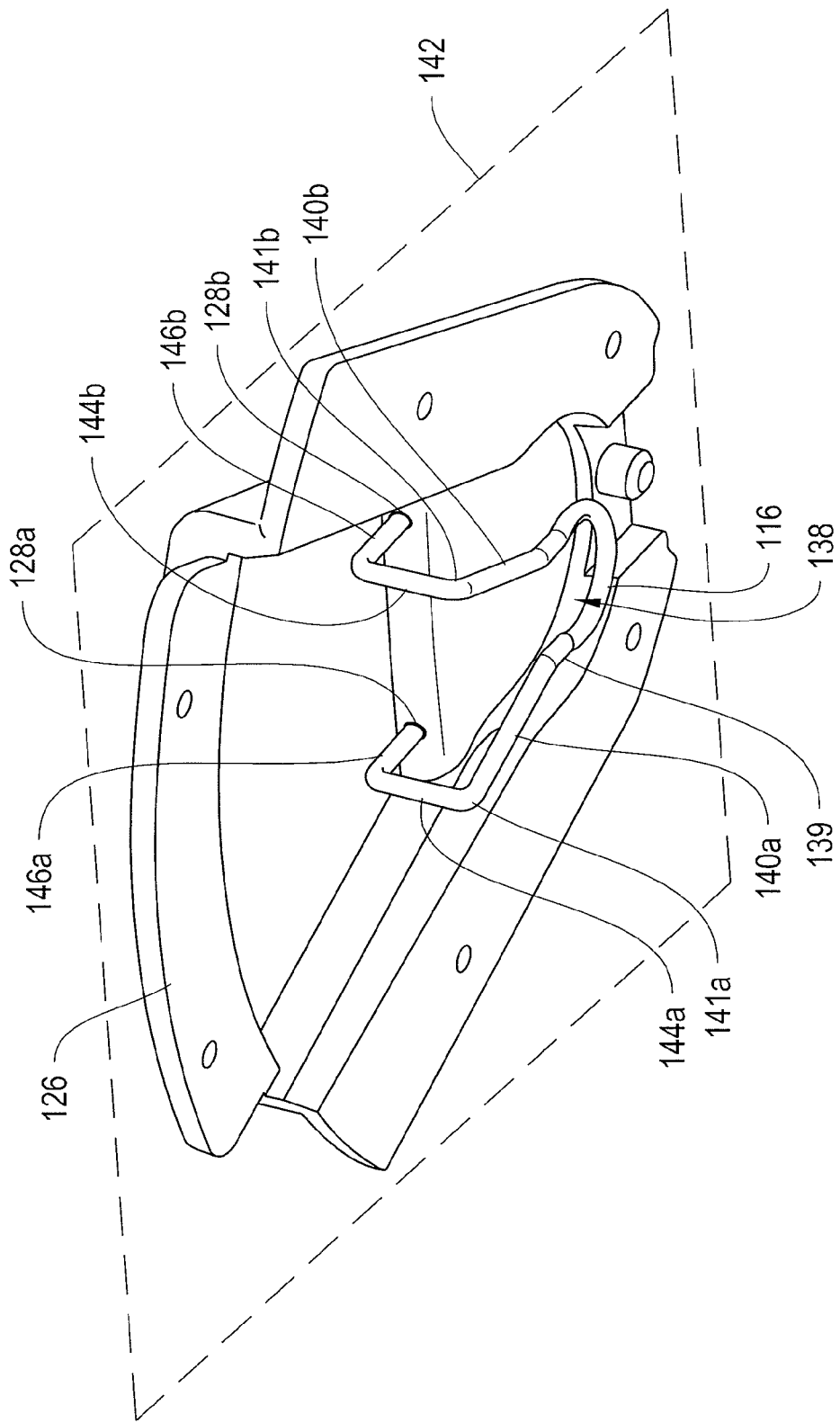
FIG. 5 shows a bottom-perspective view of a receptacle connected to a electrode connector.

In certain implementations, the receptacle 116 includes one or more compressible legs that are operable by a release actuation to adjust the size of the channel and, thereby, insertion and release of the electrode. As shown in FIG. 5, the receptacle 116 includes a pair of guide legs 140a and 140b, an electrode receiving pocket 138 for receiving and making electrical connection with the stud 104, and a neck portion 139 that bridges the guide legs to the electrode receiving pocket 138. As shown, the guide legs 140a and 140b and the electrode receiving pocket 138 are depicted in relation to a plane 142, which is substantially parallel to the bottom surface 110 of the housing 106. The guide legs 140a and 140b taper from their respective open ends 141a and 141b toward the neck portion 139. This shape helps to channel the stud 104 towards the electrode receiving pocket 138 during the engagement process. The receptacle 116 is made of spring steel wire that opens and closes responsive to the direction and the amount of the force applied. For example, as the stud 104 travels along the guide legs 140a and 140b, the stud 104 forces open the guide legs 140a and 140b slightly outwardly to create space for the stud 104 to travel and enter the electrode receiving pocket 138. The receptacle 116 also includes a pair of vertical post legs 144a and 144b that extend perpendicular to the working plane 142 and a pair of upper legs 146a and 146b that connect the vertical post legs 144a and 144b to the receptacle connector 126. These vertical post legs are spaced apart from one another initially and are configured to maintain space between the legs throughout operation. As shown in FIG. 5, the upper legs 146a and 146b are received by holes 128a and 128b and extend substantially parallel to the working plane 142. In some embodiments, the guide channel 114 extends between the guide legs 140a and 140b and the upper legs 146a and 146b.

Figure 6A:
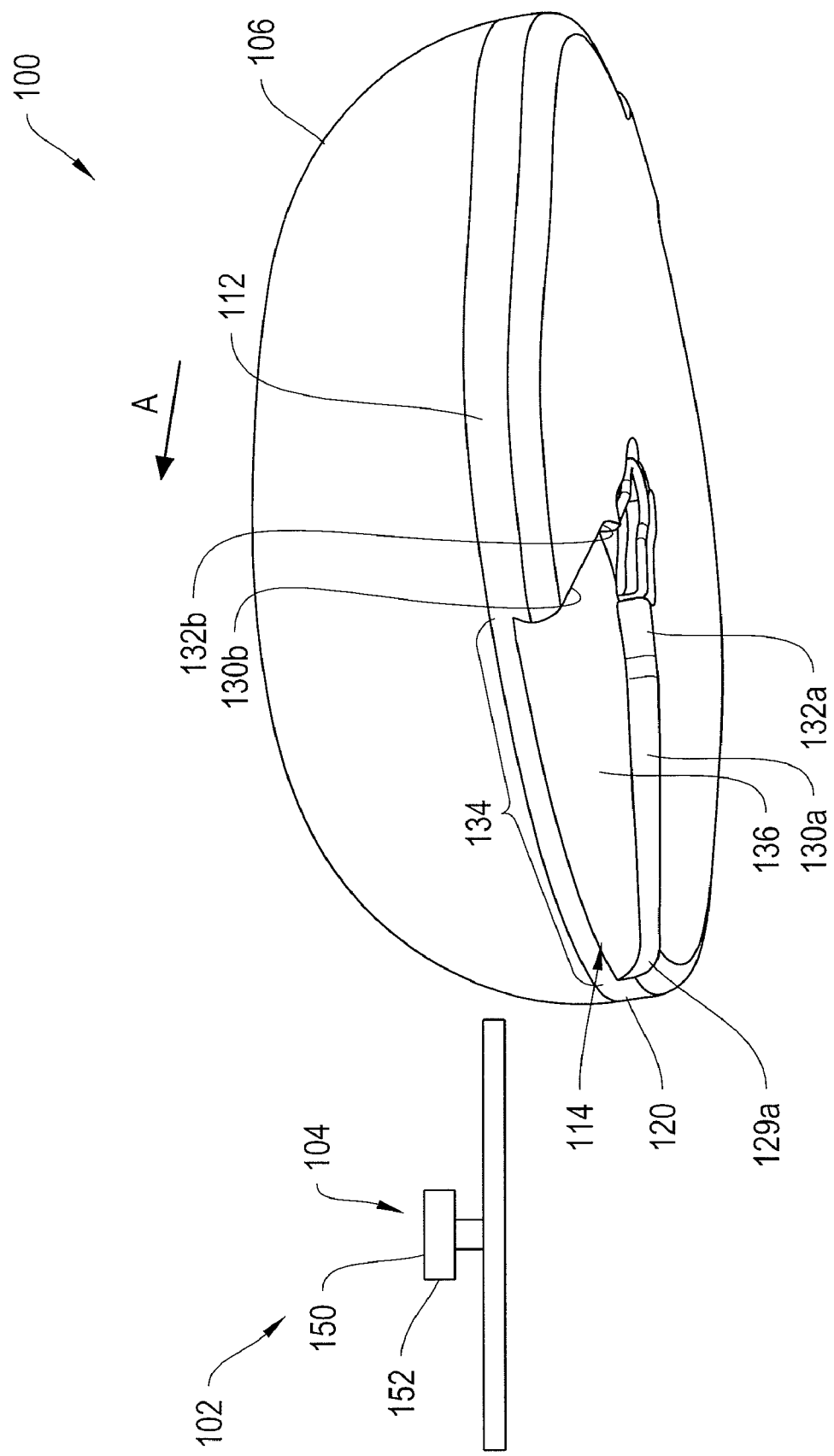

When the user is ready to apply electro-stimulation to a desired body site, the electrode 102 is placed on the user's body site and the connector 100, which may be wirelessly programmed, is initially positioned near the electrode 102. FIG. 6A shows a perspective view of the connector 100 ready to engage the electrode 102. As shown, the housing 106 includes an entry region 134 defined by the side entry guide channel 114 with opening 120. The entry region 134 receives the electrode 102 when the user initially engages the connector 100 to the electrode 102. The entry region 134 is shaped to capture the stud 104 without the user having to closely align the connector 100 with respect to the electrode 102.

Figure 6B:
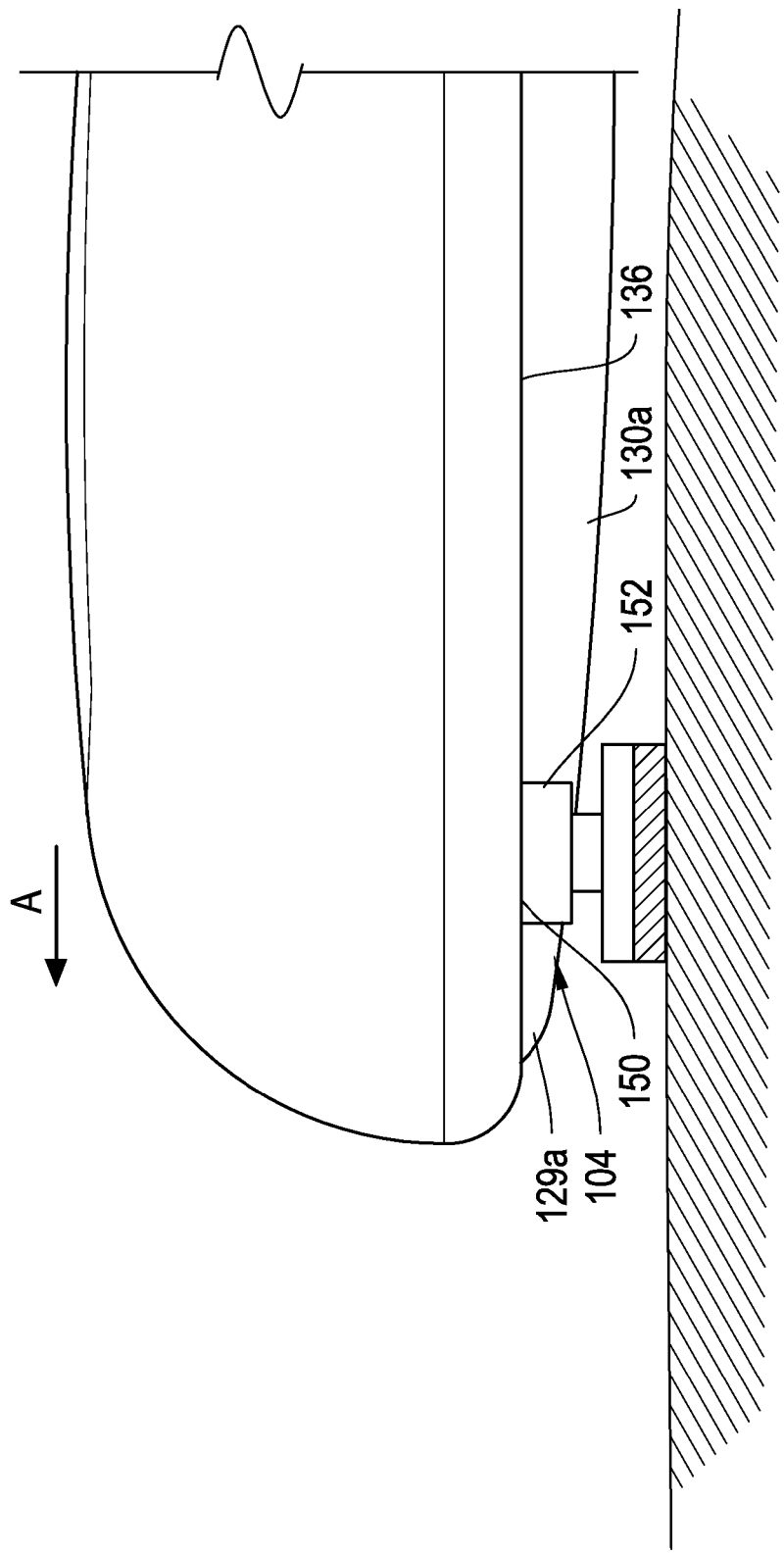

In operation, the user brings the connector 100 near the electrode 102 and slides the connector 100 laterally towards the electrode 102 so that stud 104 passes through opening 120. Initially, the electrode 102 is received by the entry region 134, which extends widely along the exterior perimeter side 112, allowing the user to roughly position the connector 100 with respect to the electrode 102. Because the entry region 134 has a large width, the user does not need to be precise when initially engaging the connector 100 to the electrode 102. This is especially helpful for users who have reduced mobility/dexterity or if the body site is located where visual contact is difficult. After the electrode 102 enters the entry region 134 through the opening 120, the channel facilitates the seating of the electrode within the connector 100 through various exemplary mechanisms. In certain implementations, a top surface 150 of the stud 104 engages an upper guiding surface 136 of the guide channel 114, as shown in FIG. 6B. As the user continues to laterally push the connector 100 towards the electrode 102 (e.g., along direction A), the upper guiding surface 136 of the connector 100 moves along the top surface 150 of the stud 104. The interior walls 130a and 130b may also act as a "rail" for the stud 104 to travel, which gives the user the feeling of tracking or guiding during the engagement process. As shown, for example, in FIG. 6C, which depicts the bottom view of the connector 100, a side surface 152 of the stud 104 may initially engage a narrow end 129a of the interior wall 130a and travels along the interior wall 130a (path P3). The stud 104 may similarly travel along the interior wall 130b and angled wall region 132b, as depicted by path P1 shown in FIG. 6C.

Alternatively, as depicted by path P2, the stud 104 may travel straight into the receptacle 116 without engaging the interior or the angled walls. As depicted by path P4, the electrode 102 may also travel along a curved path. These paths are depicted for illustrative purpose only. The electrode 102 may travel in any combination of straight and curved paths within the guide channel 114. Once the electrode 102 is guided and positioned within the receptacle 116, the user may hear an audible click or, in some embodiments, a visual indicator (e.g., ON/OFF light) provided on the top cover 118 of the connector 100 to indicate that the device is ready to be used.

Figure 7:
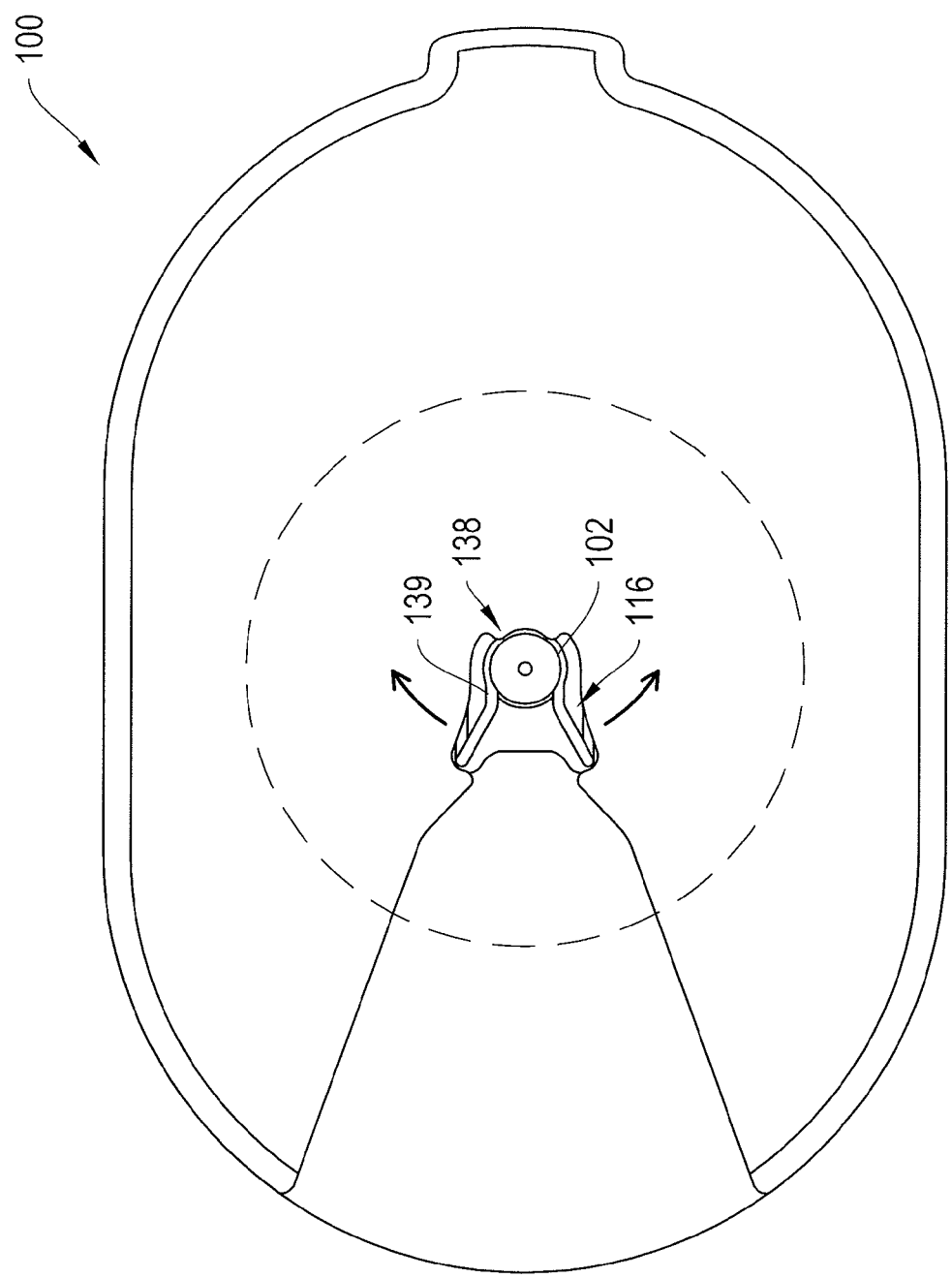
FIG. 7 shows the electrode of FIG. 5 received within a connector.

FIG. 7 shows an exemplary bottom view of the electrode 102 fully engaged to the receptacle 116 that is housed within the connector 100. As shown, the stud portion 104 of the electrode is sized such that it can be received within the electrode receiving pocket 138 of receptacle 116. Together with the neck portion 139, the shape and size of the electrode receiving pocket 138 secure the electrode 102 while the device is in use.

Figure 8:
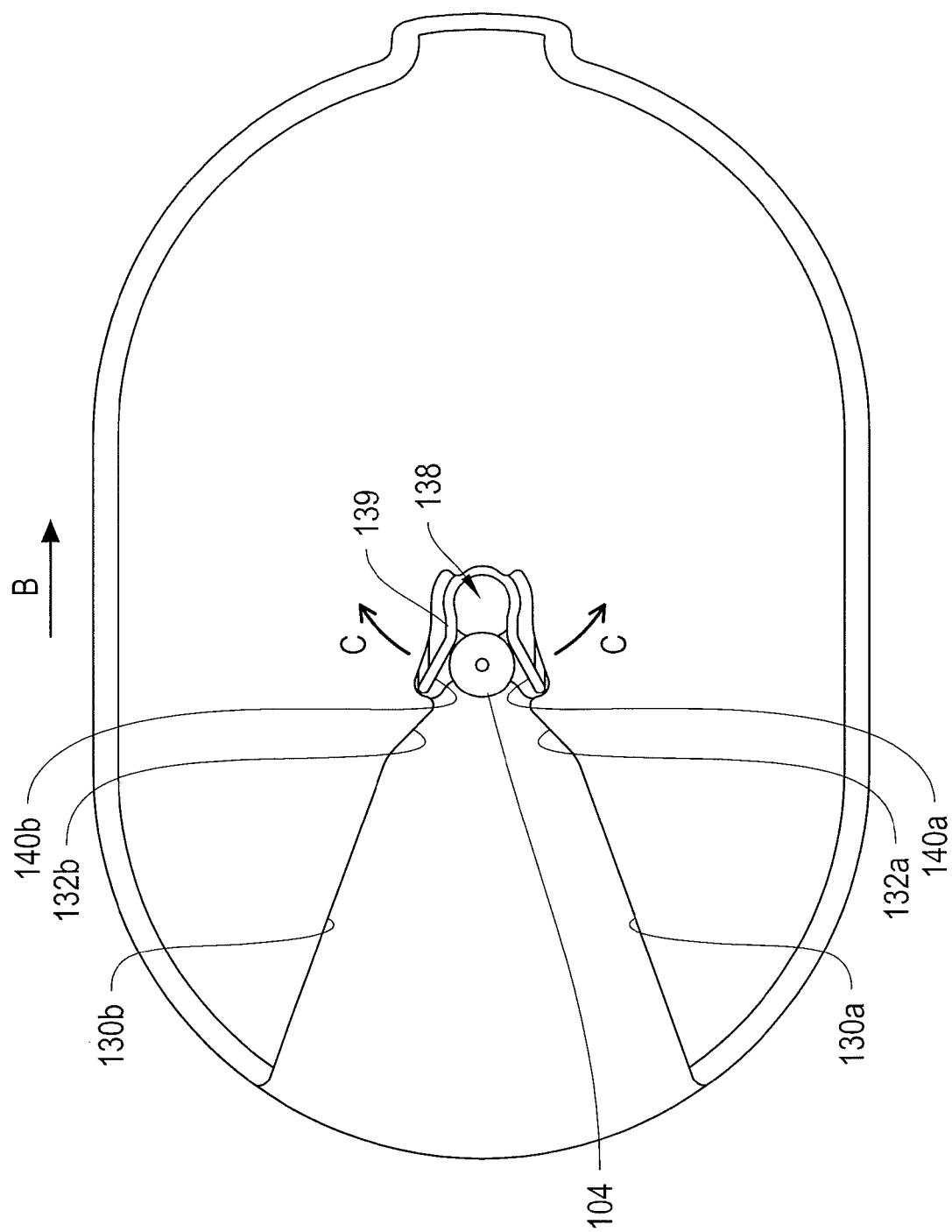
FIG. 8 shows the connector and electrode of FIG. 7 being disengaged from one another.

When the user is ready to disengage the connector 100 from the electrode 102, the connector 100 is laterally pulled away from the electrode 102 along the guide channel 114 in a direction opposite to the engagement direction. This pulling motion disengages and removes the electrode 102 from the receptacle 116. In particular, as shown in FIG. 8, when the connector 100 is pulled along direction B, the stud 104 releases from the electrode receiving pocket 138 as the pulling force exceeds the retaining force of the neck portion 139. As that occurs, the guide legs 140a and 140b open outwardly (see Arrows C depicting the outward direction) and release the stud 104 from the guide legs 140a and 140b. The stud 104 then travels along the interior wall 130a or 130b following the release. Alternatively, and similar to the entry path (e.g., P1-P4) depicted in FIG. 6C, the electrode 102 may exit the guide channel 114 along the upper guiding surface 136, the interior walls 130a or 130b, or the angled wall region 132a or 132b. In some embodiments, after the housing 106 is laterally pulled away from the electrode, the housing 106 is disengaged vertically as soon as the stud 104 is released from the guide legs 140a and 140b.

The ease of engaging and disengaging the connector 100 from the electrode 102 may vary, depending on the stiffness, size, and shape of the material that form the receptacle 116. In some embodiments, the receptacle 116 has a constant diameter throughout the part, which may range from about 0.4 mm to about 1 mm. The diameter may be smaller or larger depending on the condition to be treated. In some embodiments, the guide legs 140a and 140b, the neck portion 139, and the electrode receiving pocket 138 have varying diameters to reduce the likelihood of premature disengagement of the connector 100 from the electrode 102. For example, the neck portion 139 may have a larger diameter than the electrode receiving pocket 138, which may enable the receptacle 116 to enclose the electrode 102 with stronger force to prevent inadvertent disengagement of the connector 100 from the electrode 102.

The user can engage and disengage the connector 100 using only one hand, as the connector 100 is easily laterally slidable towards and away from the electrode 102 without requiring the user to first orient the connector 100 with respect to the electrode 102. The top cover 118 of the connector 100 may be ergonomically shaped to provide grip surfaces for the user to hold and manipulate the connector 100. The top cover 118 may be screwed or glued to the housing 106. The top cover 118 and the housing 106 are preferably made of plastic or any other suitable material that provides adequate protection to inner components housed within the housing 106. The top cover 118 may be snap fitted to the housing 106.

Figure 9A:
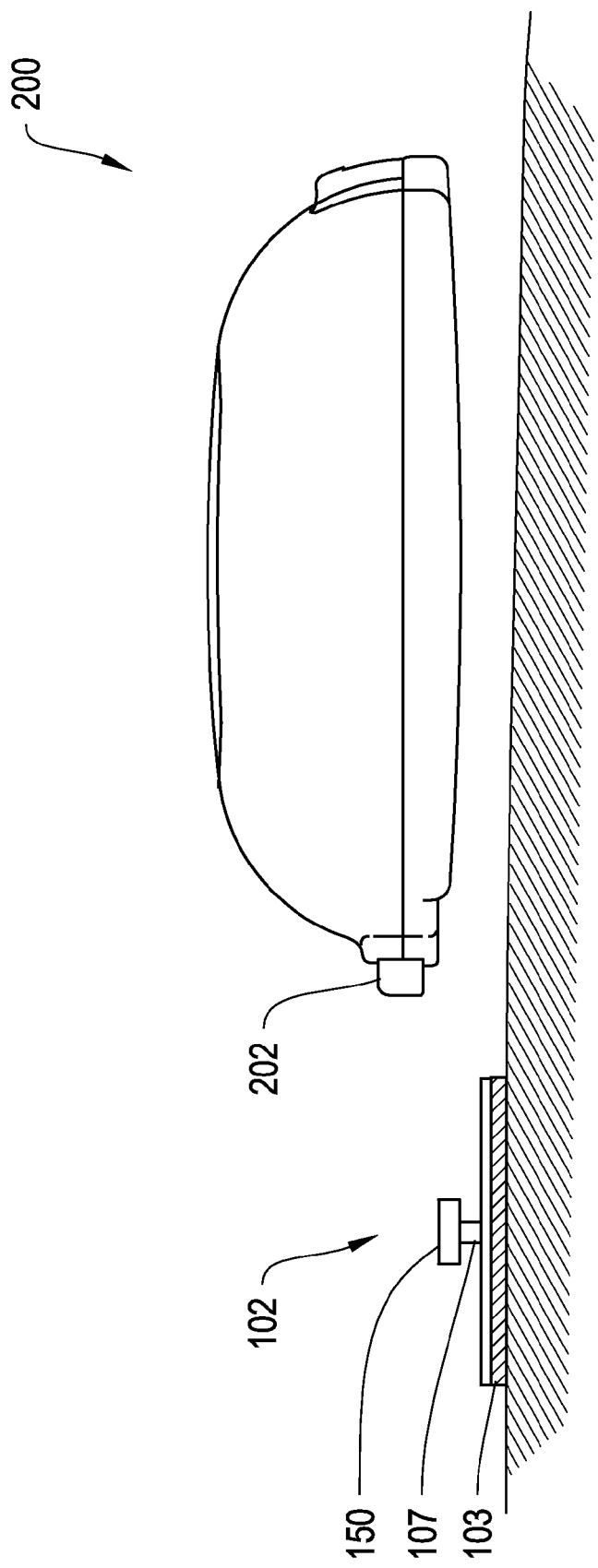
FIG. 9A shows an alternative embodiment of a connector having a release actuator engaging an electrode.
Figure 9B:
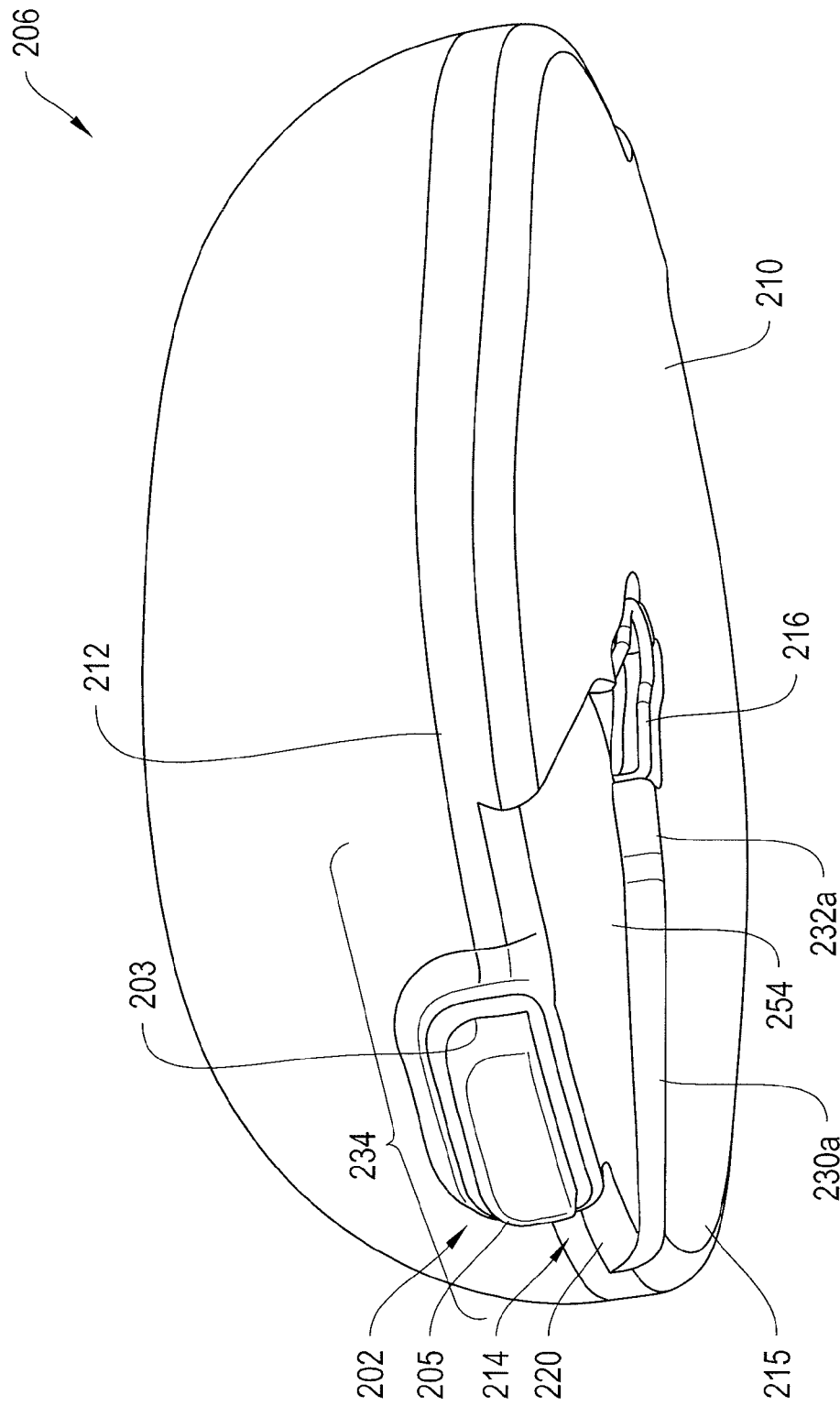
FIG. 9B shows a bottom-perspective view of the connector of FIG. 9A.

FIGS. 9A and 9B show an electrical connector 200 including a release actuator 202 for opening and closing a receptacle 216 to thereby engage and disengage the electrode 102. Similar to the connector 100, the connector 200 engages the electrode 102 by laterally traveling along the user's body site. The connector 200 includes a housing 206 having a bottom surface 210, a top surface 208, an exterior perimeter side 212, and a side-entry guide channel 214 having an opening 220 for receiving and guiding the electrode 102. The guide channel 214 also includes interior walls 230a and 230b, angled walls region 232a and 232b, and an upper guiding surface 254 for guiding the electrode 102 towards the receptacle 216, similar to the engagement described earlier with respect to the electrode 102 and the connector 100.

Figure 9C:
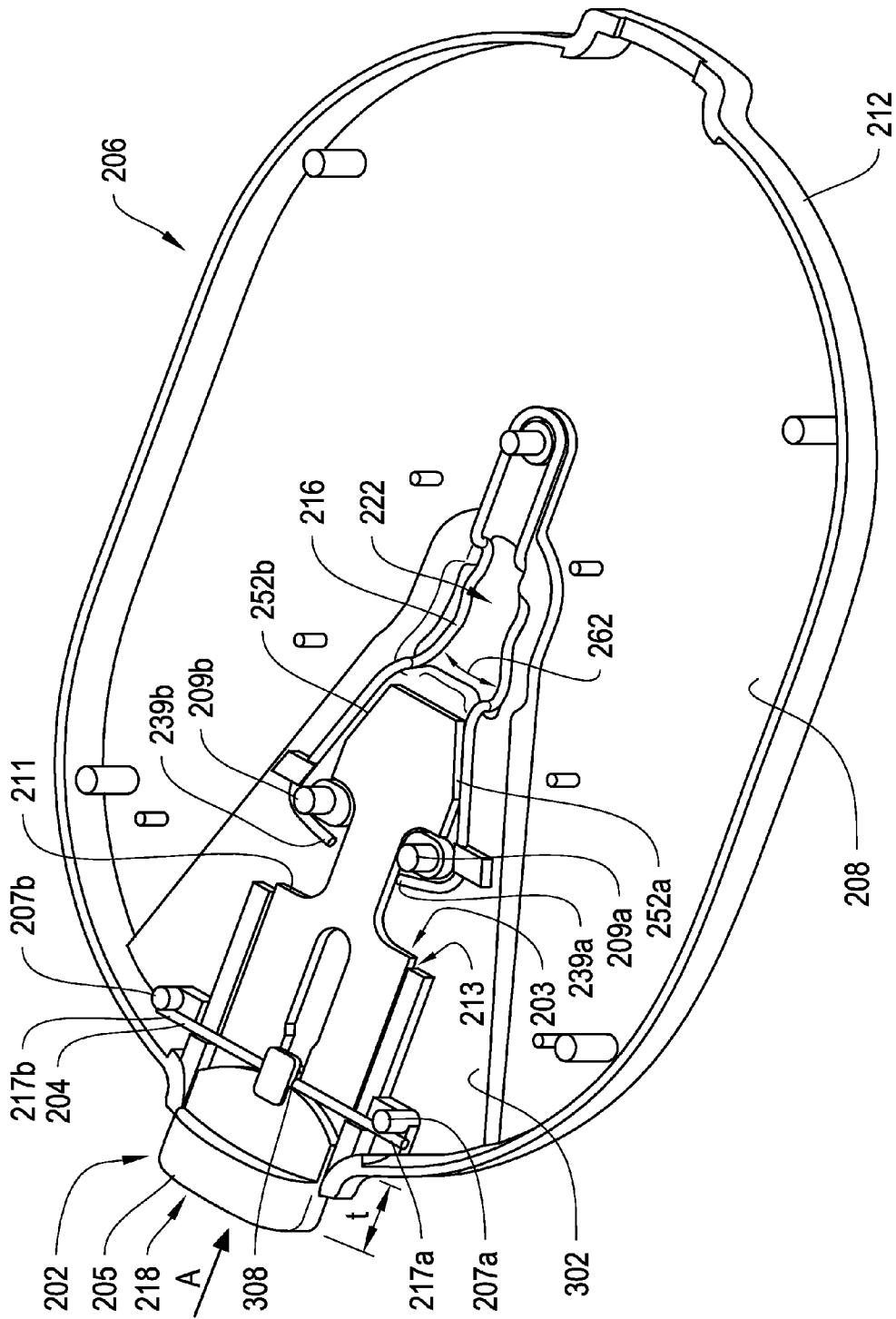
FIG. 9C shows a top-perspective view of the connector as shown in FIG. 9B without a top cover.

As shown, the release actuator 202 is engaged to the receptacle 216 near the opening 220 and when actuated, it applies a force along a plane substantially parallel with the guide channel 214 to disengage the electrode 102 from the receptacle 216. As more particularly shown in FIG. 9B-9C, the release actuator 202 is operable between open (i.e., actuated) and closed (i.e., non-actuated) positions. In the closed position, the release actuator 202 is not actuated, thus no force is applied by the release actuator 202. However, the release actuator 202 is preferably biased to stay in the closed position. As shown in FIG. 9C, the housing 206 includes an actuator slot 203 configured to house the release actuator 202. The actuator slot 203 may be disposed through the exterior perimeter side 212 of the housing 206. The actuator slot 203 includes an entry end 218, an exit end 211, and an actuator receiving surface 213 that extends between the entry end and the exit end. The release actuator 202 slides along the actuator receiving surface 213. In the closed position (shown in FIG. 9C), a release button 205 of the release actuator 202 protrudes distance t from the exterior perimeter side 212, which allows the user to tactilely locate the push button 205 even when the connector is positioned in a non-visible body part. The distance t represents the maximum travel distance of the release actuator 202 during use. As illustrated, the push button 205 has a low profile, which allows the user to place the connector 200 anywhere around the user's body and reduce the likelihood of inadvertently actuating the push button 205 when moving.

The release actuator 202 is secured to the connector 200 by biasing bar 204, which connects to receiving pocket 308 and top surface 302. The biasing bar 204 is made of an elastic material such as steel wire that allows the biasing bar 204 to be bent when force is applied and return to its original shape when the force is removed. The two ends 217a and 217b of the biasing bar 204 rest against a pair of anchoring posts 207, which are fixedly connected to the top surface 208 of the housing 206. As shown, the center portion of the biasing bar 204 is received within the bar receiving pocket 308 of the release actuator 202 anchor the bar 204 to the housing 206. The release actuator 202 is movable with respect to the housing 206.

When the user is ready to engage the connector 200 to the electrode 102 to begin the electro-stimulation, the user may actuate a push button 205 of the release actuator 202 along the direction denoted by Arrow A (FIG. 9C) to open the legs of receptacle 216 so it receives the electrode 102.

Figure 9D:
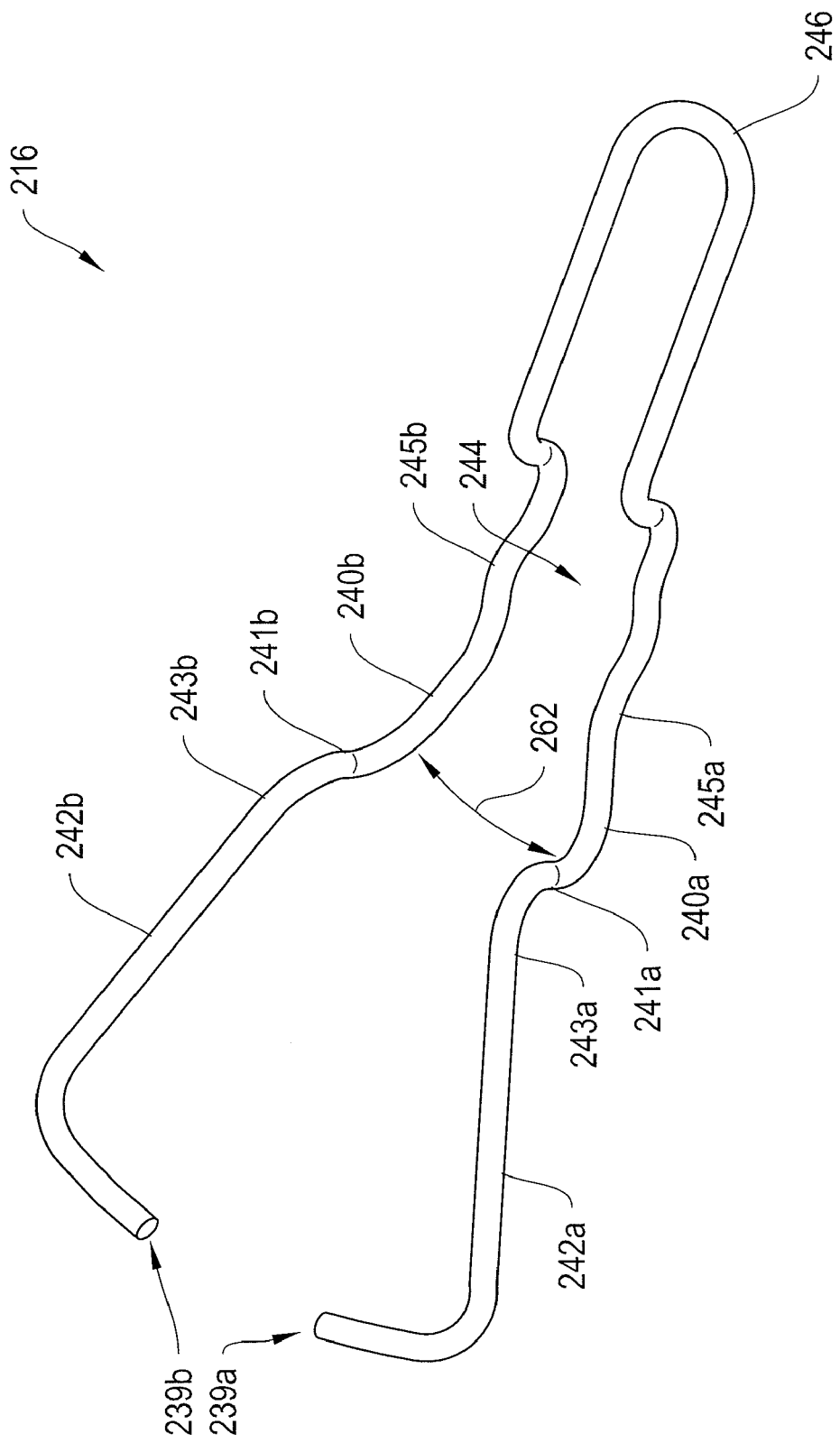
FIG. 9D shows a perspective view of an exemplary receptacle housed within the connector of FIG. 9C.
Figure 9E:
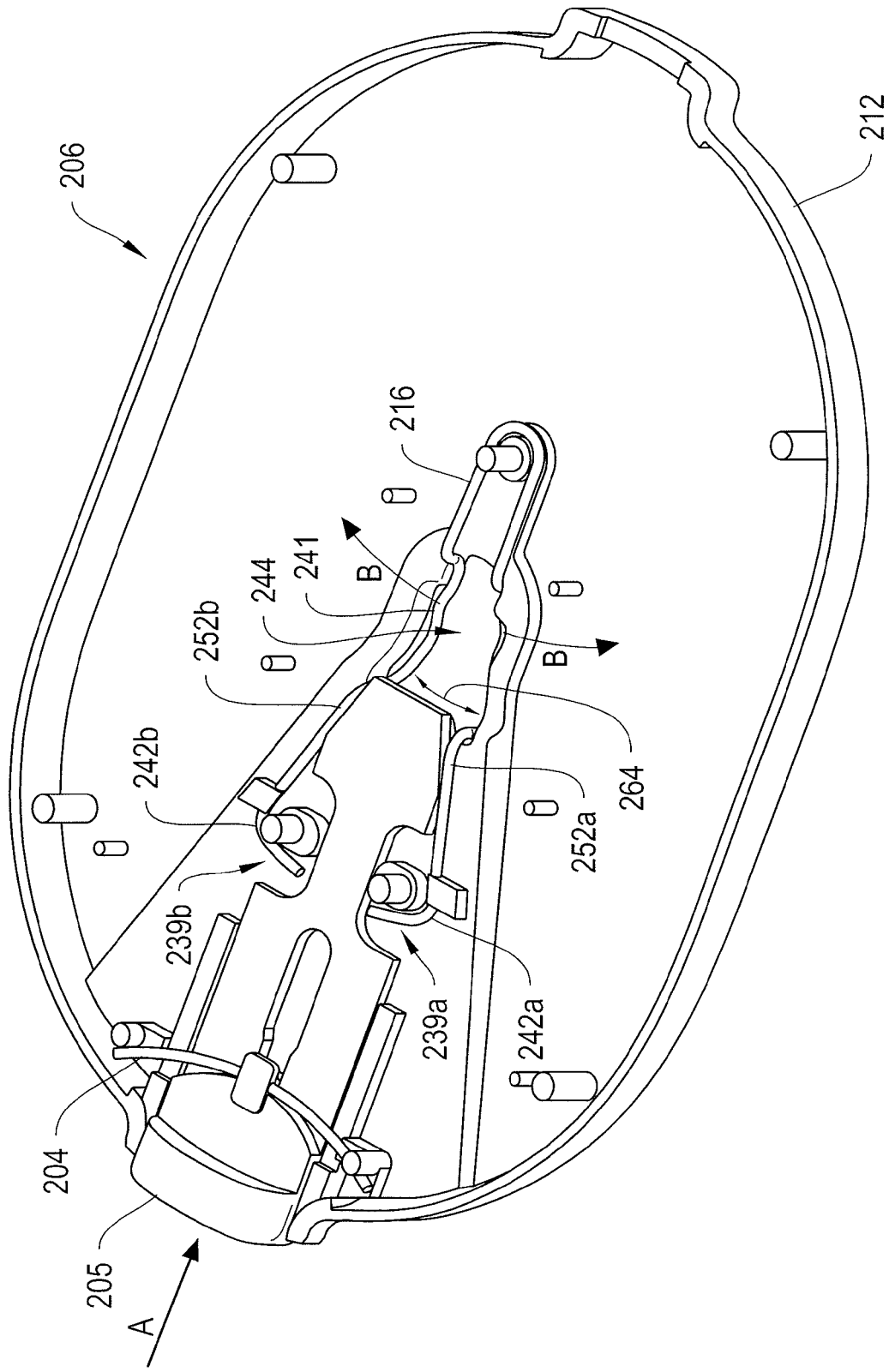
FIG. 9E shows a top-perspective view of the connector of FIG. 9C with the release actuator depressed.

As further illustrated in FIGS. 9C-9E, the release actuator 202 laterally engages and actuates the receptacle 216 to open and close, thereby receiving and releasing the electrode. The receptacle 216, which is made of steel or other conducting wires, includes free ends 239a and 239b that are disconnected from one another. Such shape and the spring characteristics of the steel wire allows the receptacle 216 to be squeezed and released. When the receptacle 216 is squeezed, the free ends 239a and 239b move closer to another. When the receptacle 216 is released from the squeezed position, the free ends retreat back to their original positions (i.e., move away from one another). As shown in FIG. 9C, the free ends 239a and 239b are bent about position posts 209a and 209b, which are fixed to the top surface 208 of the housing 206. These posts 209a and 209b help align the receptacle 216 when the device is in use. The free ends 239a and 239b also connect to a pair of upper legs 242a and 242b, respectively. As shown, the free ends 239a and 239b and the upper legs 242a and 242b extend along a plane that is substantially parallel to the top surface 208. In some embodiments, the free ends and/or the upper legs are disposed in a plane that is at an angle with respect to the top surface 208. The free ends may also be bent at an angle with respect to the upper legs. The upper legs 242a and 242b are connected to the guide legs 240a and 240b, respectively, via connecting legs 241a and 241b. As shown, the guide legs 240a and 240b and the upper legs 242a and 242b lie in a plane that is substantially parallel but spaced away from one another. The connecting legs 241a and 241b are fitted within a receptacle pocket 222 (FIG. 9C) that is sized to house the guide legs 240a and 240b and the electrode receiving pocket 244 of the receptacle 216.

The release actuator 202 includes contact surfaces 252a and 252b that engage the corresponding contact portions 243a and 243b of the upper legs 242a and 242b when the release actuator 202 is actuated. When the user depresses the button 205 of the actuator 202, the contact surfaces 252a and 252b of the actuator 202 engage and push the upper legs 242a and 242b of the receptacle 216 away from one another in the direction denoted by Arrows B (FIG. 9E). When this happens, the upper legs 242a and 242b move the guide legs 240a and 240b along the same direction to make room for the electrode 102 to pass through passageway 262, which extends between the guide legs 240a and 240b. The guide legs 240a and 240b are initially spaced apart and are configured to maintain this spacing until the release actuator 202 is actuated to open the passageway a distance 262. As noted above, the guide legs 240a and 240b are connected to the electrode receiving pocket 244, which is sized and shaped to receive and engage the stud 104 of the electrode 102 during the electro-stimulation. The electrode receiving pocket 244 is connected to an anchoring end 246 for receiving a fastener (e.g., screw) to connect the receptacle 216 to the housing 206.

FIG. 9E shows an embodiment of the release actuator 202 opening the receptacle 216 when the user has pushed the push button 205 until it is flush with the exterior perimeter side 212 of the housing 206. When this happens, the passageway 262 is widened to 264 thereby allowing the electrode 102 to pass through the receptacle 216 more easily. As shown, the free ends 239a and 239b are moved further apart from one another, the electrode receiving pocket 244 is enlarged to receive the stud 104 of the electrode 102. While holding down the push button 205, the user may experience some resistance applied by the biasing bar 204. As shown in FIG. 9E, the biasing bar 204 is bowed slightly against the force applied by the user via the push button 205. In some embodiments, the user may hold down the push button 205 while laterally moving the connector 200 against the user's body site. As described above, actuating the push button 205 opens the receptacle 216 to receive the stud 104 of the electrode 102. As the connector 200 approaches near the electrode 102 laterally, the electrode 102 is received within the guide channel 214 and is guided by the various walls of the guide channel 214 to the electrode receiving pocket 244 of the receptacle 216. After the electrode 102 is engaged to the receptacle, the user may release the push button 205. When the button is released, which is biased against the spring force of the biasing bar 204, the release actuator 202 returns to its original position as shown in FIG. 9C. This forces the contact surfaces 252a and 252b of the release actuator 202 to retreat backwards to its original position and disengage contact with the corresponding contact portions 243a and 243b of the receptacle 216, thereby narrowing the passageway 264 to 262. With the stud 104 of the electrode 102 engaged within the electrode receiving pocket 244, when the passageway returns to its original configuration, it acts as a gate that encloses the stud 104. In some embodiments, the stud 104 is held within the electrode receiving pocket 244 until the release actuator 202 is actuated again to open the receptacle 216. Following the completion of the electro-stimulation, the user may actuate the release actuator 202 to disengage the connector 200 from the electrode 102. Upon actuating the release actuator 202, the electrode 102 is removed from the receptacle 216 when the housing 206 is pulled away from the electrode 102 along the guide channel 214.

In some embodiments, the user may "force" open the receptacle 216 during engagement. Similar to the connection between connector 100 and the electrode 102, the user may take the connector 200 and laterally push along the user's body site without first actuating the release actuator 202. In such configuration, manual force applied by pushing the connector 200 against the stud 104 of the electrode is sufficient to force open the receptacle 216. Similar to the engagement between the connector 100 and the electrode 102 (FIG. 6A), the stud 104 is initially received within the guide channel 214 and it travels along the interior walls 230a and/or 230b and angled walls 232a and/or 232b. The stud 104 is further guided to the electrode receiving pocket 244 via guide legs 240a and 240b. The force applied by the user opens the guide legs 240a and 240b and the stud 104 is pushed into the electrode receiving pocket 244. The connector 200 is now ready for use. Following the completion of the electro-stimulation, the user may actuate the release actuator 202, which enlarges the opening between the guide legs 240a and 240b, to disengage the connector 200 from the electrode 102. The user may also manually pull the connector 200 opposite the engagement direction. Using the release actuator 202 to disengage the connector 200 may apply less force to the user's treatment area, which may be beneficial to users with sensitive skin or wound, particularly where the electrode is applied to that sensitive skin or wound area.

In some embodiments, the connectors 100 and 200 connect and disconnect vertically over the stud 104. In such configuration, the connector is positioned near the stud 104 which includes a narrow waist 107 (FIG. 9A) disposed between the top surface 150 and the active surface 103. The narrow waist 107 of the electrode 102 receives a portion of pocket wires 245a and 245b (FIG. 9D) when the connector is pushed vertically downward near the stud 104 during the engagement. When the user is ready to disengage the connector 100 or 200 from the electrode 102, the connector 100 or 200 is vertically pulled away from the electrode 102. This vertical pulling motion disengages the pocket wires 245a and 245b from the narrow waist 107 of the electrode 102 and releases the electrode 102 from the connector 100 or 200.

Figure 10:
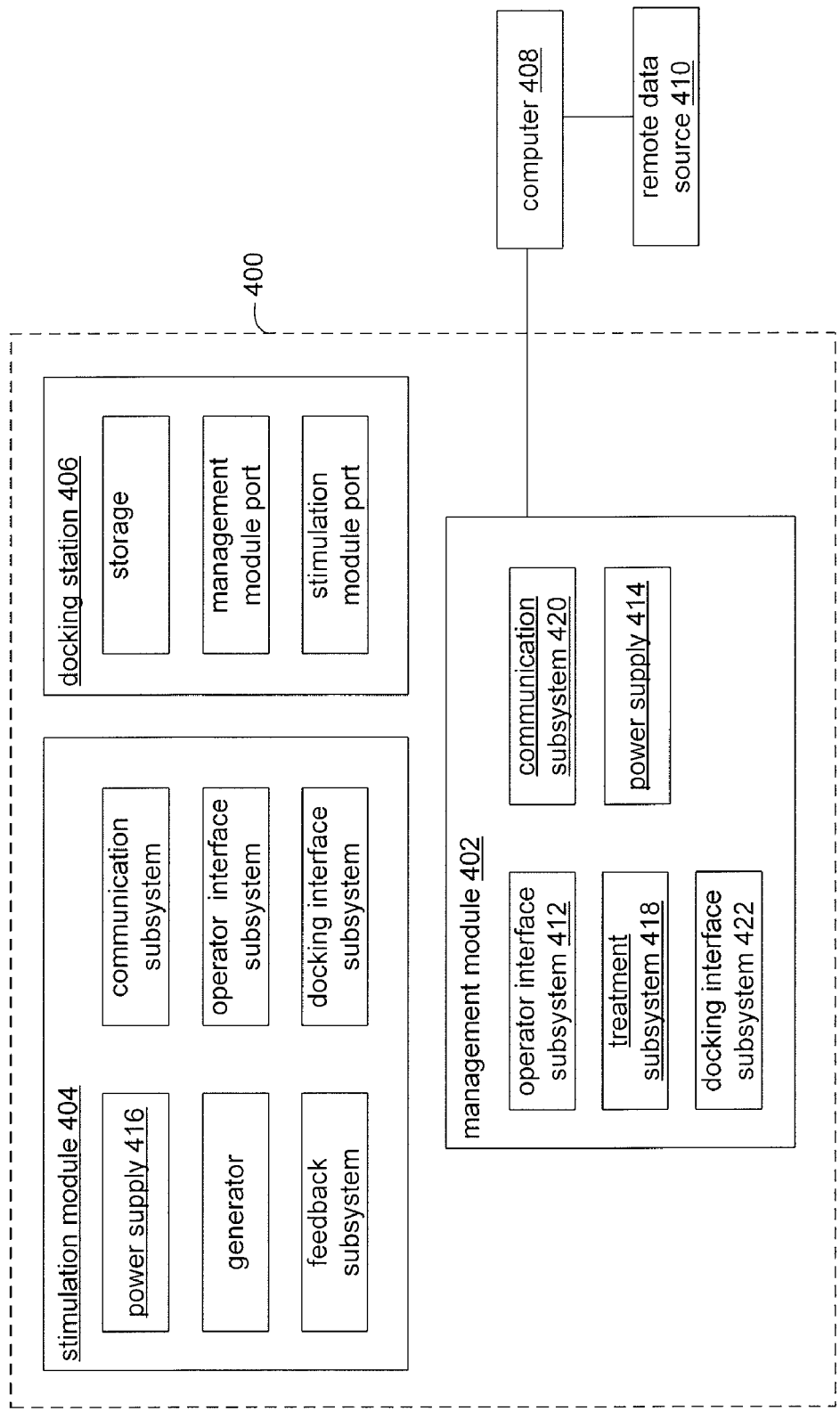
FIG. 10 is a block diagram of an illustrative electrostimulation system.

In certain implementations, the connectors 100 and 200 include, among other things, a battery, a controller, an electrical circuitry, and a transceiver for receiving and sending data such as a treatment protocol to apply electrical stimulation to a user's body site. The transceiver is also configured to receive and/or transmit signals to a control device for stimulating nerves. FIG. 10 is a block diagram of an electrical stimulation system 400, in accordance with certain embodiments. The system 400 includes a control module 402, a stimulation module 404 and a docking station 406. The diagram of FIG. 10 also includes a computer 408 which is capable of communicating with a remote data source 410.

In certain implementations, the control module 402 provides an interface between the stimulation module 404 and an operator who wishes to control therapy applied to a user. An operator may be a care provider or the user him/herself. The control module 402 may transmit and receive information to and from the stimulation module 404 via a wireless communication protocol. The control module 402 may also allow an operator to navigate through an operator interface, select stimulation programs or protocols, set desired options and control the waveforms applied to the user. The control module 402 may also be capable of interfacing with the computer 408 in order to access the remote data source 410.

FIG. 10 depicts a number of subsystems that may be included in the control module 402. In certain implementations, an operator interface subsystem 412 allows an operator to adjust the treatment provided to a user by the system 400, view current operating parameters, view historical user data (such as performance and use statistics), view current physiological parameters (such as muscle feedback signals), and adjust the capabilities of the system 400 (e.g., by downloading additional programs to the control module 402 from the remote data source 410).

The control module 402 includes a power supply 414. The power supply 414 may be any suitable source of energy for powering the components of the control module 402. The power supply 414 may be a battery, or an AC power supply (such as a standard wall power supply). The power supply 414 may include a solar cell, a thermal cell or a kinetic cell capable of converting motion energy to electrical energy for powering the control module 102. It will be noted that the control module 402 may contain multiple power supplies, any of which may be any of the power supplies described herein.

The control module 402 (as well as any device or system component described herein) may include memory for storing basic operating parameters (e.g., pre-stored sounds, volume, display parameters, time and date) and/or supporting any of the subsystems described in detail below. The control module 402 may use memory for storing statistics regarding usage of the control module 402. For example, information such as type of program, date and frequency of treatments, and intensities applied may be recorded in memory. In an embodiment, usage statistics are uploadable from memory to the remote data source 410 when the control module 402 is in communication with the remote data source 410 (e.g., via the computer 408).

The control module 402 may include a treatment subsystem 418. The treatment subsystem 418 may include circuitry for communicating with any one or more of the other subsystems and components of the control module 402, including the operator interface subsystem 412, the communication subsystem 420, and the feedback subsystem 422. The treatment subsystem 418 may include memory for storing one or more stimulation protocols and/or programs for electrical stimulation. The memory coupled to the treatment subsystem 418 is capable of storing at least 15 different stimulation protocols or programs.

It is to be understood that the forgoing description is merely illustrative. While several embodiments have been provided in the present disclosure, it should be understood that the disclosed systems, components, and methods may be embodied in many other specific forms without departing from the scope of the present disclosure.

The invention is not to be limited to the details given herein but variations and modifications will occur to those of skill in the art after reviewing this disclosure. The disclosed features may be implemented in sub-combinations with one or more other features described herein. For example, a variety of systems and methods may be implemented based on the disclosure and still fall within the scope. Also, the various features described or illustrated above may be combined or integrated in other systems or certain features may be omitted, or not implemented.

Examples of changes, substitutions, and alterations are ascertainable by one skilled in the art and could be made without departing from the scope of the information disclosed herein. Certain particular aspects, advantages, and modifications are within the scope of the following claims. All references cited herein are incorporated by reference in their entirety and made part of this application.

What is claimed is:

1. A low profile electrical connector for connecting to an electro-stimulation element comprising:
    a housing having exterior perimeter sides and top and bottom surfaces, and wherein the bottom surface is configured to extend along a user's body site and the top surface is spaced above the bottom surface;
    a first side-entry guide channel disposed along the bottom surface, the channel having an opening along the exterior perimeter side that is configured to receive an electrically conductive element, the channel being disposed beneath the top surface such that the top surface forms an upper guiding surface for an electrically conductive element, and the channel having at least two interior walls, wherein the upper guiding surface and at least two interior walls are configured to guide the electrically conductive element along the first side-entry guide channel; and
    a receptacle positioned within the housing and disposed between the at least two interior walls, the receptacle having a receiving pocket with an electrically conductive surface that forms an electrical interface with the electrically conductive element, and at least one guide leg configured to guide the electrically conductive element from the first side-entry guide channel to the receiving pocket.

2. The low profile electrical connector of claim 1, wherein the at least one guide leg comprises a pair of guide legs that taper toward the receiving pocket of the receptacle.

3. The low profile electrical connector of claim 2, wherein the receptacle comprises a neck region that bridges the guide legs and the receiving pocket of the receptacle.

4. The low profile electrical connector of claim 3, wherein the receiving pocket is spaced away from the walls of the guide channel.

5. The low profile electrical connector of claim 4, wherein the receptacle is formed of a wire.

6. The low profile electrical connector of claim 1, wherein the height of the interior walls increases from the opening toward the receptacle.

7. The low profile electrical connector of claim 6, wherein the upper guiding surface extends at an acute angle with respect to the bottom surface of the housing.

8. The low profile electrical connector of claim 1, wherein the upper guiding surface extends parallel to the bottom surface of the housing.

9. The low profile electrical connector of claim 8, wherein the guide channel is defined at least in part by the bottom surface of the housing.

10. The low profile electrical connector of claim 1, wherein during disengagement the housing is pulled away from the electrically conductive element along at least one of the at least two interior walls.

11. The low profile electrical connector of claim 10, wherein the at least two interior walls form a path that tapers into the receptacle.

12. The low profile electrical connector of claim 1, wherein the at least one guide leg comprises at least two guide legs, and wherein the receptacle includes at least two upper legs and at least two vertically disposed post legs, the vertically disposed post legs being spaced apart from one another and configured to maintain space between the at least two guide legs throughout operation.

13. The low profile electrical connector of claim 12, comprising a release actuator configured to release the electrically conductive element from the receptacle, the release actuator laterally engaged to the receptacle and adapted to move the at least two upper legs of the receptacle away from one another in response to the actuation of the release actuator.

14. The low profile electrical connector of claim 13, wherein the side-entry guide channel extends between the at least two guide legs and the at least two upper legs.

15. The low profile electrical connector of claim 1, wherein the housing includes a transceiver that is configured to receive and/or transmit signals to a control device for stimulating muscle or nerve.

16. The low profile electrical connector of claim 1, comprising a plurality of side-entry guide channels disposed along the exterior perimeter side, wherein each of said side-entry guide channels is configured for receiving an electrically conductive element.

17. The low profile electrical connector of claim 16, comprising a plurality of receptacles positioned within the housing, each receptacle disposed to receive an electrically conductive element.

18. The low profile electrical connector of claim 16, wherein the plurality of side-entry guide channels connect to the receptacle.

19. The low profile electrical connector of claim 1, wherein pulling the housing vertically away from the electrically conductive element removes the electrically conductive element from the receptacle.

20. The low profile electrical connector of claim 1, wherein the electrically conductive element is an electrode.

21. A method of configuring an electro-stimulation connector comprising:
providing an electrical connector with a housing having exterior perimeter sides and top and bottom surfaces, wherein the bottom surface is configured to extend along a plane where an electrically conductive element is positioned and the top surface is spaced away from the bottom surface, and wherein
a side-entry guide channel is disposed along the bottom surface, the channel having an opening along the exterior perimeter side that is configured to receive an electrically conductive element, the channel being disposed beneath the top surface such that the top surface forms an upper guiding surface for an electrically conductive element, and the channel having at least two interior walls configured to guide the electrically conductive element along the side-entry guide channel;
sliding the housing along the plane to receive the electrically conductive element through the opening and to pass the electrically conductive element along the guide channel to a receiving pocket within a receptacle, the receiving pocket having an electrical contact site, and the receptacle being positioned within the housing and having at least one guide leg configured to guide the electrically conductive element from the side-entry guide channel to the receptacle.

22. The method of claim 21, wherein the housing comprises a release actuator operatively engaged to the receptacle, wherein actuating the release actuator disconnects connection between the receptacle and the electrically conductive element, and upon actuating the release actuator the electrically conductive element is removed from the receptacle when the receptacle is pulled away from the electrically conductive element along the guide channel.

23. The method of claim 21, wherein the electrically conductive element is an electrode.

24. The method of claim 21, further comprising laterally sliding the receptacle away from the electrically conductive element along the guide channel to disengage and remove the receptacle from the electrically conductive element.

25. The method of claim 24, wherein the guide channel has at least two interior walls that extend from the opening toward the receptacle, and wherein laterally sliding the housing away from the electrically conductive element along at least one of the at least two interior walls disconnects the receptacle from the electrically conductive element.

26. A low profile electrical connector for connecting to an electro-stimulation element comprising:
a housing having exterior perimeter sides and top and bottom surfaces, wherein the bottom surface is configured to extend along a user's body site and the top surface is spaced above the bottom surface;
a receptacle positioned within the housing and having a guide leg configured to guide an electrically conductive element to the receptacle, and an electrically conductive surface that forms an electrical interface with the electrically conductive element;
a first side-entry guide channel disposed along the bottom surface, the channel having an opening along the exterior perimeter side that is configured to receive the electrically conductive element, the channel including at least two interior walls that form a path that tapers from the opening into the receptacle, and the channel being configured to guide the electrically conductive element within the housing.

27. The low profile electrical connector of claim 26, wherein the at least two interior walls form a V-shaped path that tapers into the receptacle.

28. The low profile electrical connector of claim 27, wherein the housing has a receptacle pocket, and the guide channel includes an angled wall region extending from each interior wall to the receptacle pocket.

29. The low profile electrical connector of claim 26, wherein the height of the interior walls increases from the opening toward the receptacle.

30. The low profile electrical connector of claim 26, wherein the guide channel is disposed beneath the top surface such that the top surface forms an upper guiding surface that extends substantially parallel to the bottom surface of the housing.

31. A low profile electrical connector for connecting to an electro-stimulation element comprising:

a housing having exterior perimeter sides and top and bottom surfaces, and wherein the bottom surface is configured to extend along a user's body site and the top surface is spaced above the bottom surface;

a plurality of side-entry guide channels disposed along the exterior perimeter sides and exposed through the bottom surface, wherein each of said side-entry guide channels has an opening along at least one of the exterior perimeter sides that is configured for receiving an electrically conductive element, the channels being configured to guide the electrically conductive element within the housing to a receptacle, the receptacle being positioned within the housing and having an electrically conductive surface that forms an electrical interface with the electrically conductive element.

32. The low profile electrical connector of claim 31, wherein each of the plurality of side-entry guide channels connects to the receptacle.

33. The low profile electrical connector of claim 31, comprising a plurality of receptacles positioned within the housing, each receptacle disposed to receive an electrically conductive element.

34. A low profile electrical connector for connecting to an electro-stimulation element comprising:

a housing having exterior perimeter sides and top and bottom surfaces, and wherein the bottom surface is configured to extend along a user's body site and the top surface is spaced above the bottom surface;

a first side-entry guide channel disposed along the bottom surface, the channel having an opening along the exterior perimeter side that is configured to receive an electrically conductive element, the channel being configured to guide the electrically conductive element within the housing;

a receptacle positioned within the housing and having an electrically conductive surface that forms an electrical interface with the electrically conductive element; and a release actuator operatively engaged to the receptacle, wherein the release actuator applies a force along a plane substantially parallel with the guide channel to disengage the electrically conductive element from the receptacle.

35. The low profile electrical connector of claim 34, wherein upon actuating the release actuator, the electrically conductive element is removed from the receptacle when the housing is pulled away from the electrically conductive element along the guide channel.

36. The low profile electrical connector of claim 34, wherein the housing includes a slot extruding through the exterior perimeter side of the housing and configured to receive the release actuator.

37. A low profile electrical connector for connecting to an electro-stimulation element comprising:

a housing having exterior perimeter sides and top and bottom surfaces, and wherein the bottom surface is configured to extend along a user's body site and the top surface is spaced above the bottom surface;

a first side-entry guide channel disposed along the bottom surface, the channel having an opening along the exterior perimeter side that is configured to receive an electrically conductive element, and the channel being configured to guide the electrically conductive element within the housing;

a receptacle positioned within the housing and having an electrically conductive surface that forms an electrical interface with the electrically conductive element, wherein the receptacle includes at least two upper legs, at least two vertically disposed post legs, and at least two guide legs configured to guide the electrically conductive element from the side-entry guide channel, the vertically disposed post legs being spaced apart from one another and configured to maintain space between the legs throughout operation.

38. The low profile electrical connector of claim 37, comprising a release actuator configured to release the electrically conductive element from the receptacle, the release actuator laterally engaged to the receptacle and adapted to move the upper legs of the receptacle away from one another in response to the actuation of the release actuator.

39. The low profile connector of claim 38, wherein the side-entry guide channel extends between the at least two guide legs and the at least two upper legs.

* * * * *

UNITED STATES PATENT AND TRADEMARK OFFICE
CERTIFICATE OF CORRECTION

PATENT NO. : 8,197,276 B2
APPLICATION NO. : 12/856382
DATED : June 12, 2012
INVENTOR(S) : Egloff et al.

Page 1 of 1

It is certified that error appears in the above-identified patent and that said Letters Patent is hereby corrected as shown below:

On the Cover Page:

(75) Inventors: first inventor city name, please replace "Lausaune" with --Lausanne--.

Signed and Sealed this
Fourteenth Day of August, 2012

David J. Kappos
*Director of the United States Patent and Trademark Office*